(12) United States Patent
Jackson

(10) Patent No.: US 8,012,177 B2
(45) Date of Patent: Sep. 6, 2011

(54) DYNAMIC STABILIZATION ASSEMBLY WITH FRUSTO-CONICAL CONNECTION

(76) Inventor: Roger P. Jackson, Prairie Village, KS (US)

( * ) Notice: Subject to any disclaimer, the term of this patent is extended or adjusted under 35 U.S.C. 154(b) by 256 days.

(21) Appl. No.: 12/456,704

(22) Filed: Jun. 19, 2009

(65) Prior Publication Data

US 2009/0281574 A1 Nov. 12, 2009

Related U.S. Application Data

(63) Continuation-in-part of application No. 12/069,577, filed on Feb. 11, 2008, now abandoned, application No. 12/456,704, which is a continuation-in-part of application No. 12/070,535, filed on Feb. 19, 2008, now abandoned, application No. 12/456,704, which is a continuation-in-part of application No. 12/287,035, filed on Oct. 3, 2008.

(60) Provisional application No. 61/132,911, filed on Jun. 24, 2008, provisional application No. 60/997,079, filed on Oct. 1, 2007, provisional application No. 60/900,816, filed on Feb. 12, 2007, provisional application No. 60/902,470, filed on Feb. 21, 2007, provisional application No. 60/999,965, filed on Oct. 23, 2007.

(51) Int. Cl.
*A61B 17/70* (2006.01)
(52) U.S. Cl. .......... 606/254; 606/246; 606/308
(58) Field of Classification Search .......... 606/246, 606/254, 305, 301, 86 A, 261, 257, 250, 251, 606/253, 264, 308, 266, 256, 265, 260, 258, 606/259; 403/292–298
See application file for complete search history.

(56) References Cited

U.S. PATENT DOCUMENTS

| 2,243,717 | A | 5/1941 | Moreira |
| 3,236,275 | A | 2/1966 | Smith |
| 3,604,487 | A | 9/1971 | Gilbert |
| 3,640,416 | A | 2/1972 | Temple |
| 4,041,939 | A | 8/1977 | Hall |
| 4,373,754 | A | 2/1983 | Bollfrass et al. |
| 4,448,191 | A | 5/1984 | Rodnyansky et al. |
| 4,484,570 | A | 11/1984 | Sutter et al. |
| 4,600,224 | A | 7/1986 | Blose |
| 4,653,486 | A | 3/1987 | Coker |
| 4,703,954 | A | 11/1987 | Ortloff et al. |
| 4,707,001 | A | 11/1987 | Johnson |
| 4,743,260 | A | 5/1988 | Burton |
| 4,748,260 | A | 5/1988 | Marlett |

(Continued)

FOREIGN PATENT DOCUMENTS

DE 4239716 8/1994

(Continued)

OTHER PUBLICATIONS

*EBI Omega 21* Brochure, EBI Spine Systems, pub. 1999.

(Continued)

*Primary Examiner* — Pedro Philogene
(74) *Attorney, Agent, or Firm* — John C. McMahon

(57) ABSTRACT

A dynamic fixation medical implant for attachment to at least two bone anchors includes a longitudinal connecting member assembly having first and second rigid sections, at least one section having a convex or frusto-conical surface held in spaced relation with the other section by an elastic spacer. The spacer may be an over-mold that connects the first and second rigid sections. Some embodiments include an inner, tougher spacer and a separate over-molded spacer.

22 Claims, 18 Drawing Sheets

U.S. PATENT DOCUMENTS

| | | |
|---|---|---|
| 4,836,196 A | 6/1989 | Park et al. |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno |
| 5,499,892 A | 3/1996 | Reed |
| 5,507,745 A | 4/1996 | Logroscino et al. |
| 5,540,688 A | 7/1996 | Navas |
| 5,545,165 A | 8/1996 | Biedermann et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,528 A | 3/1998 | Biedermann et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| RE36,221 E | 6/1999 | Breard et al. |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,143,032 A | 11/2000 | Schafer et al. |
| 6,146,383 A | 11/2000 | Studer et al. |
| 6,183,472 B1 | 2/2001 | Lutz |
| RE37,161 E | 5/2001 | Michelson et al. |
| 6,224,596 B1 | 5/2001 | Brace et al. |
| 6,224,598 B1 | 5/2001 | Jackson |
| 6,235,034 B1 | 5/2001 | Bray |
| 6,241,730 B1 * | 6/2001 | Alby ............................ 606/256 |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |

| Patent | Date | Inventor |
|---|---|---|
| 6,402,757 B1 | 6/2002 | Moore et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Doono et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,029,475 B2 | 4/2006 | Panjabi |
| 7,125,410 B2 | 10/2006 | Freudiger |
| 7,137,985 B2 | 11/2006 | Jahng |
| 7,207,992 B2 | 4/2007 | Ritland |
| 7,229,441 B2 | 6/2007 | Trieu et al. |
| 7,294,129 B2 | 11/2007 | Hawkins et al. |
| 7,326,210 B2 * | 2/2008 | Jahng et al. .................. 606/86 A |
| 7,329,258 B2 * | 2/2008 | Studer ........................... 606/250 |
| 7,361,196 B2 | 4/2008 | Fallin et al. |
| 7,377,921 B2 | 5/2008 | Studer et al. |
| 7,476,238 B2 | 1/2009 | Panjabi |
| 7,828,823 B2 * | 11/2010 | Rogeau et al. ................. 606/256 |
| 7,828,824 B2 * | 11/2010 | Kwak et al. .................... 606/257 |
| 2001/0001119 A1 | 5/2001 | Lombardo |
| 2001/0010000 A1 | 7/2001 | Gertzbein |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0082602 A1 | 6/2002 | Biedermann et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0171749 A1 | 9/2003 | Le Douedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |

| | | |
|---|---|---|
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Johng |
| 2005/0070899 A1 | 3/2005 | Doubler et al. |
| 2005/0080415 A1 | 4/2005 | Keyer et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0079896 A1 | 4/2006 | Kwak |
| 2006/0079898 A1 | 4/2006 | Ainsworth |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom |
| 2006/0085069 A1 | 4/2006 | Kim |
| 2006/0106381 A1 | 5/2006 | Ferree |
| 2006/0122599 A1 | 6/2006 | Drewry |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer |
| 2006/0149229 A1 | 7/2006 | Kwak |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |

| | | |
|---|---|---|
| 2006/0189985 A1 | 8/2006 | Lewis |
| 2006/0195090 A1 | 8/2006 | Suddaby |
| 2006/0195093 A1 | 8/2006 | Jahng |
| 2006/0200130 A1 | 9/2006 | Hawkins |
| 2006/0212033 A1 | 9/2006 | Rothman |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0241769 A1 | 10/2006 | Gordon |
| 2006/0241771 A1 | 10/2006 | Gordon |
| 2006/0247632 A1 | 11/2006 | Winslow |
| 2006/0247633 A1 | 11/2006 | Winslow |
| 2006/0247635 A1 | 11/2006 | Gordon |
| 2006/0247637 A1 | 11/2006 | Colleran |
| 2006/0247779 A1 | 11/2006 | Gordon |
| 2006/0264935 A1 | 11/2006 | White |
| 2006/0264937 A1 | 11/2006 | White |
| 2006/0264940 A1 | 11/2006 | Hartmannt |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293663 A1 | 12/2006 | Walkenhorst |
| 2007/0005062 A1 | 1/2007 | Lange |
| 2007/0005063 A1 | 1/2007 | Bruneau |
| 2007/0005137 A1 | 1/2007 | Kwak |
| 2007/0016190 A1 | 1/2007 | Martinez |
| 2007/0016193 A1 | 1/2007 | Ritland |
| 2007/0043356 A1 | 2/2007 | Timm |
| 2007/0049936 A1 | 3/2007 | Colleran |
| 2007/0055236 A1 | 3/2007 | Hudgins |
| 2007/0055247 A1 | 3/2007 | Jahng |
| 2007/0073289 A1 | 3/2007 | Kwak |
| 2007/0073293 A1 | 3/2007 | Martz |
| 2007/0078461 A1 | 4/2007 | Shluzas |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0100341 A1 | 5/2007 | Reglos et al. |
| 2007/0118119 A1 | 5/2007 | Hestad |
| 2007/0118122 A1 | 5/2007 | Butler et al. |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161991 A1 | 7/2007 | Altarac et al. |
| 2007/0161997 A1 | 7/2007 | Thramann et al. |
| 2007/0173818 A1 | 7/2007 | Hestad et al. |
| 2007/0173822 A1 | 7/2007 | Bruneau et al. |
| 2007/0173832 A1 | 7/2007 | Tebbe et al. |
| 2007/0191841 A1 | 8/2007 | Justis et al. |
| 2007/0191846 A1 | 8/2007 | Bruneau et al. |
| 2007/0213720 A1 | 9/2007 | Gordon et al. |
| 2007/0225708 A1 | 9/2007 | Biedermann et al. |
| 2007/0225710 A1 | 9/2007 | Jahng et al. |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233085 A1 | 10/2007 | Biedermann et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0270814 A1 | 11/2007 | Lim et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0276380 A1 | 11/2007 | Jahng et al. |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0033435 A1 | 2/2008 | Studer et al. |
| 2008/0039843 A1 | 2/2008 | Abdou |
| 2008/0045951 A1 | 2/2008 | Fanger et al. |
| 2008/0051787 A1 | 2/2008 | Remington et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0125777 A1 | 5/2008 | Veldman et al. |
| 2008/0125787 A1 | 5/2008 | Doubler et al. |
| 2008/0140133 A1 | 6/2008 | Allard et al. |
| 2008/0154307 A1 | 6/2008 | Colleran et al. |
| 2008/0161854 A1 | 7/2008 | Bae et al. |
| 2008/0167687 A1 | 7/2008 | Colleran et al. |
| 2008/0177316 A1 | 7/2008 | Bergeronk et al. |
| 2008/0177319 A1 | 7/2008 | Schwab |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0195100 A1 | 8/2008 | Capote et al. |
| 2008/0215095 A1 | 9/2008 | Biedermann et al. |
| 2008/0221620 A1 | 9/2008 | Krause |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Wabler et al. |
| 2008/0234736 A1 | 9/2008 | Trieu et al. |
| 2008/0234737 A1 | 9/2008 | Boschert |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0300630 A1 | 12/2008 | Bohnema et al. |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2009/0005817 A1 | 1/2009 | Friedrich et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |

| | | | |
|---|---|---|---|
| 2009/0099608 A1 | 4/2009 | Szczesny | |
| 2009/0105760 A1 | 4/2009 | Frey | |
| 2009/0112265 A1 | 4/2009 | Hudgins et al. | |
| 2009/0112266 A1 | 4/2009 | Weng et al. | |
| 2009/0112267 A1 | 4/2009 | Atkinson et al. | |
| 2009/0118767 A1 | 5/2009 | Hestad et al. | |
| 2009/0125063 A1 | 5/2009 | Panjabi | |
| 2009/0131981 A1 | 5/2009 | White | |

FOREIGN PATENT DOCUMENTS

| | | |
|---|---|---|
| DE | 4425392 | 11/1995 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 9202745.8 | 4/1992 |
| GB | 2365345 | 2/2002 |
| GB | 2382304 | 5/2003 |
| JP | 10277070 | 10/1998 |
| JP | 2000325358 | 3/2000 |
| WO | WO92/03100 | 3/1992 |
| WO | WO94/10927 | 5/1994 |
| WO | WO94/26191 | 11/1994 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/012088 | 2/2006 |
| WO | WO2006/017616 | 2/2006 |
| WO | WO2006/028537 | 3/2006 |
| WO | WO2006/045094 | 4/2006 |
| WO | WO2007/002409 | 1/2007 |
| WO | WO2007124249 | 11/2007 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |

OTHER PUBLICATIONS

*Claris Instrumentation* Brochure, G Med, pub. 1997.
*VLS System Variable Locking Screw* Brochure, Interpore Cross International, 1999.
*The Rod Plate* System Brochure, Stryker Howmedica Osteonics, pub. Oct. 1999.
*SDRS Surgical Dynamics Rod System* Brochure, Surgical Dynamics, pub. 1998-1999.
*Versalok Low Back Fixation System* Brochure, Wright Medical Technology, Inc., pub. 1997.
Brochure of Tyco/Healthcare/Surgical Dynamics on Spiral Radius 90D, Publication Date: Sep. 2001, pp. 1-8.

\* cited by examiner

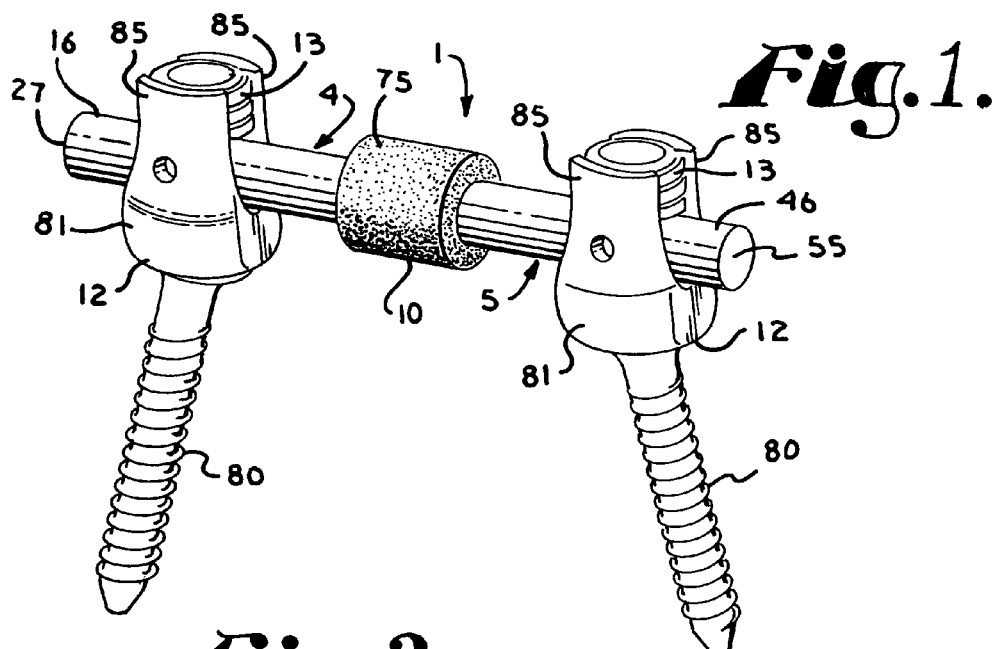
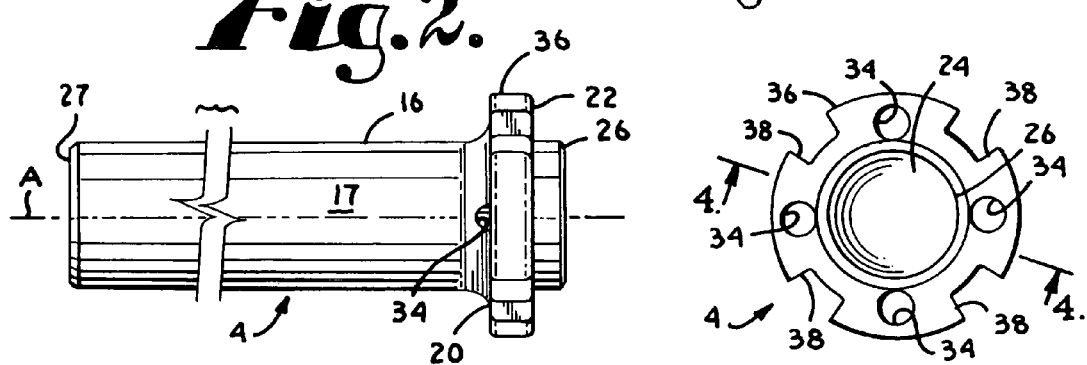
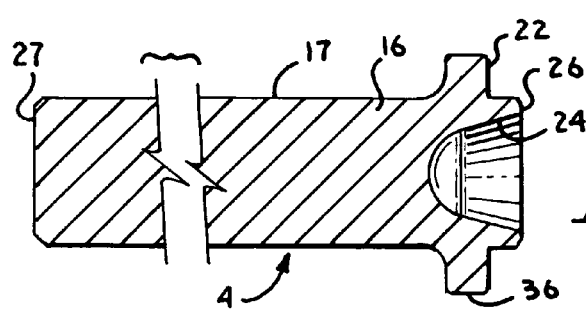

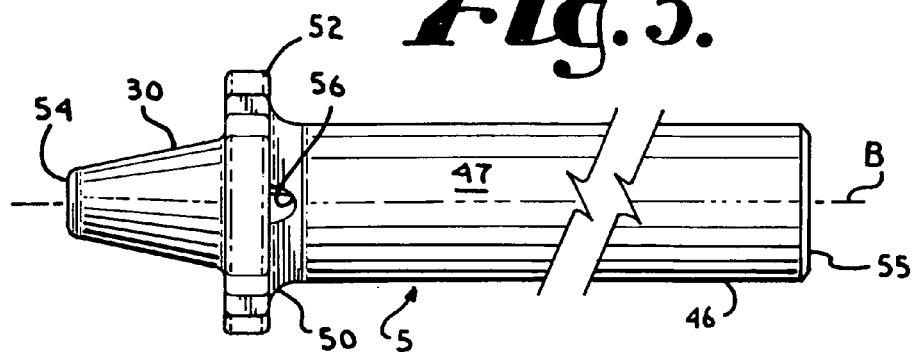
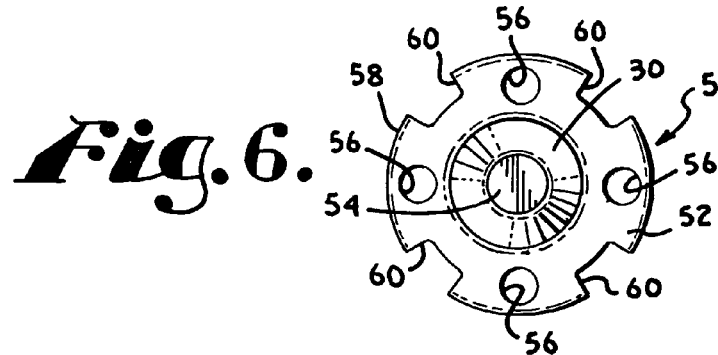
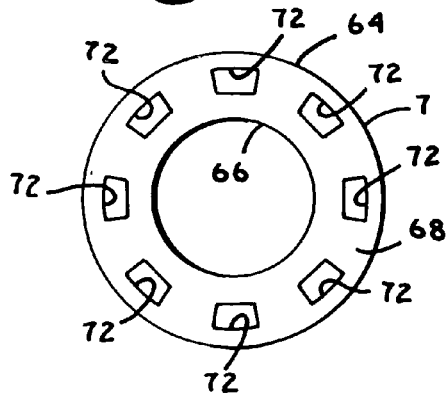
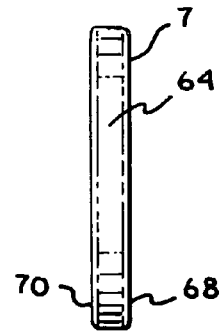

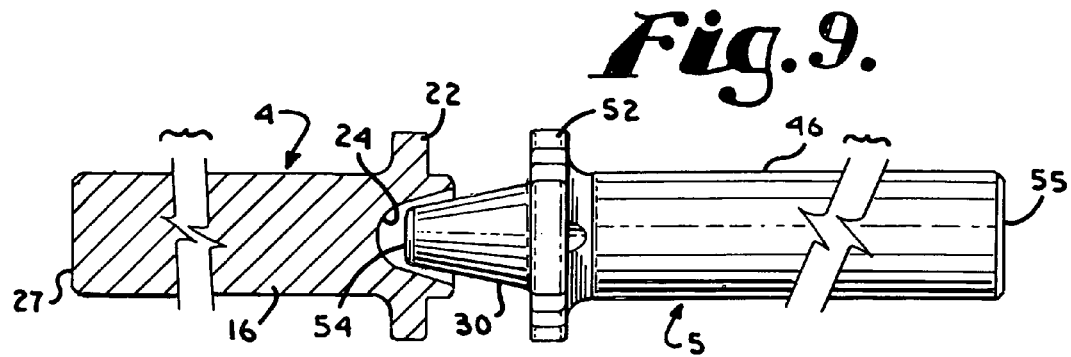
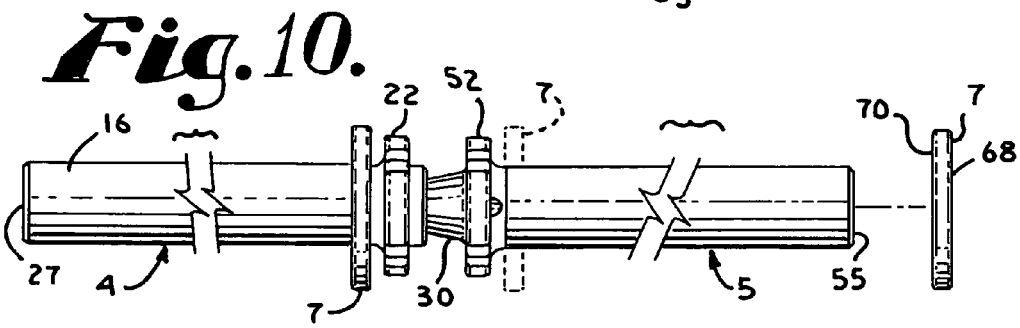
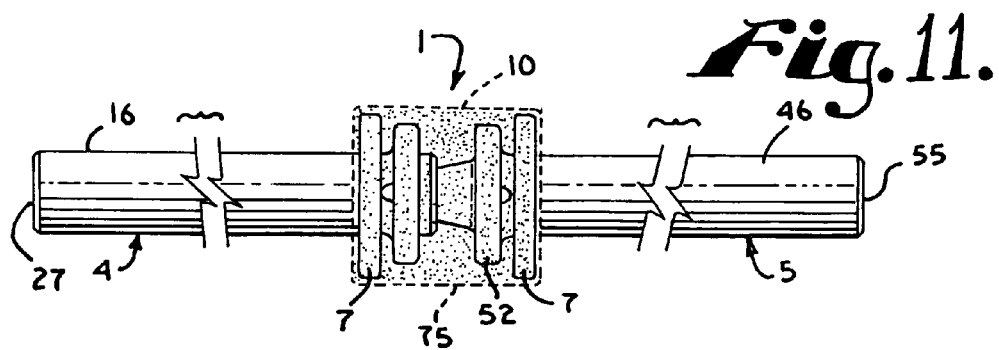
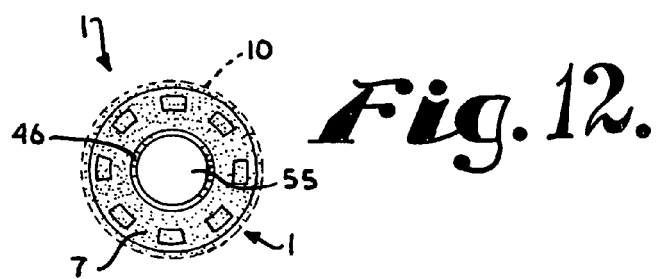

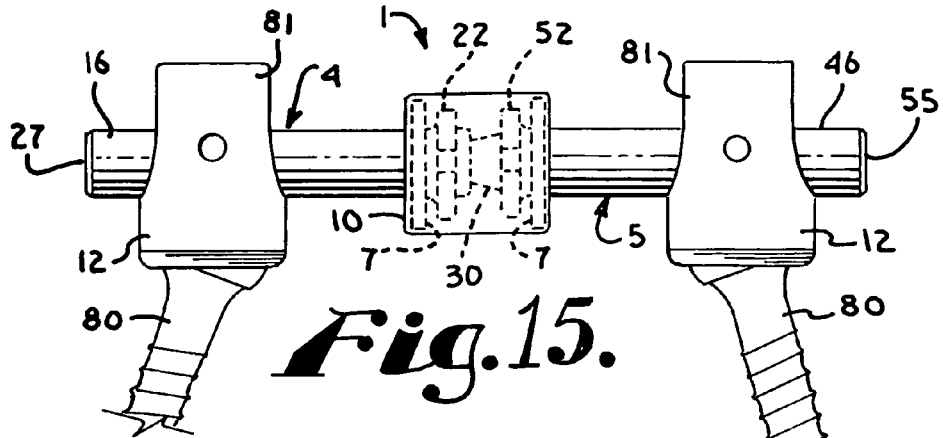
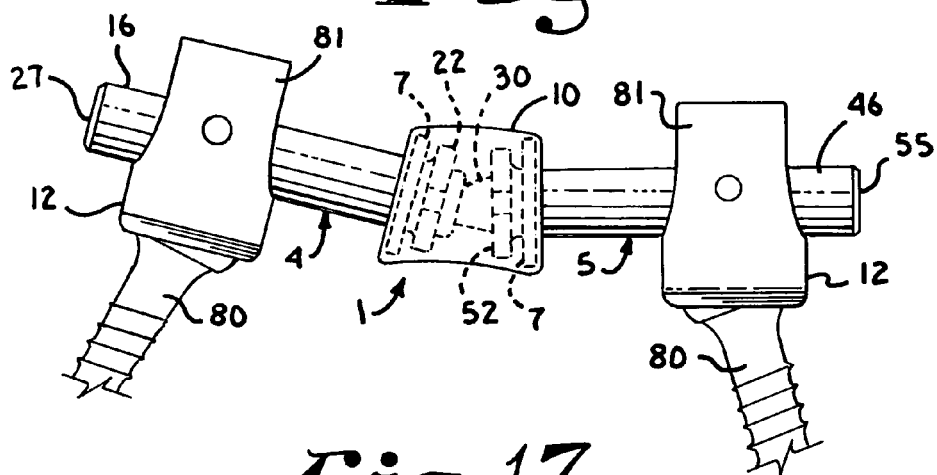
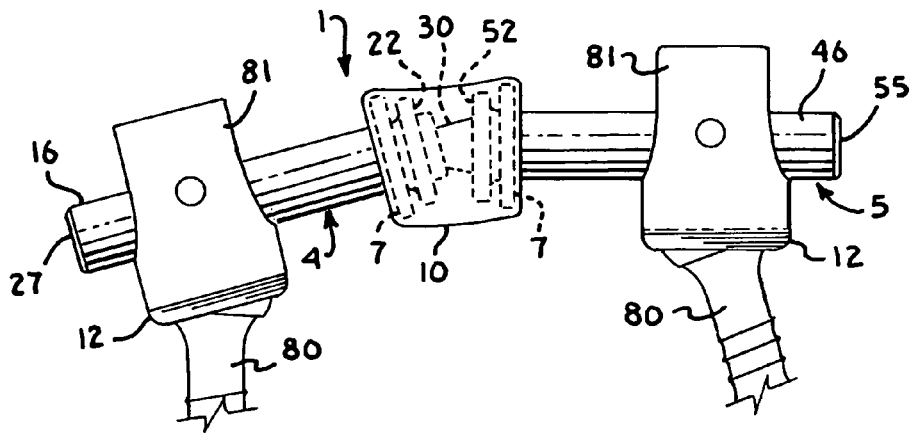

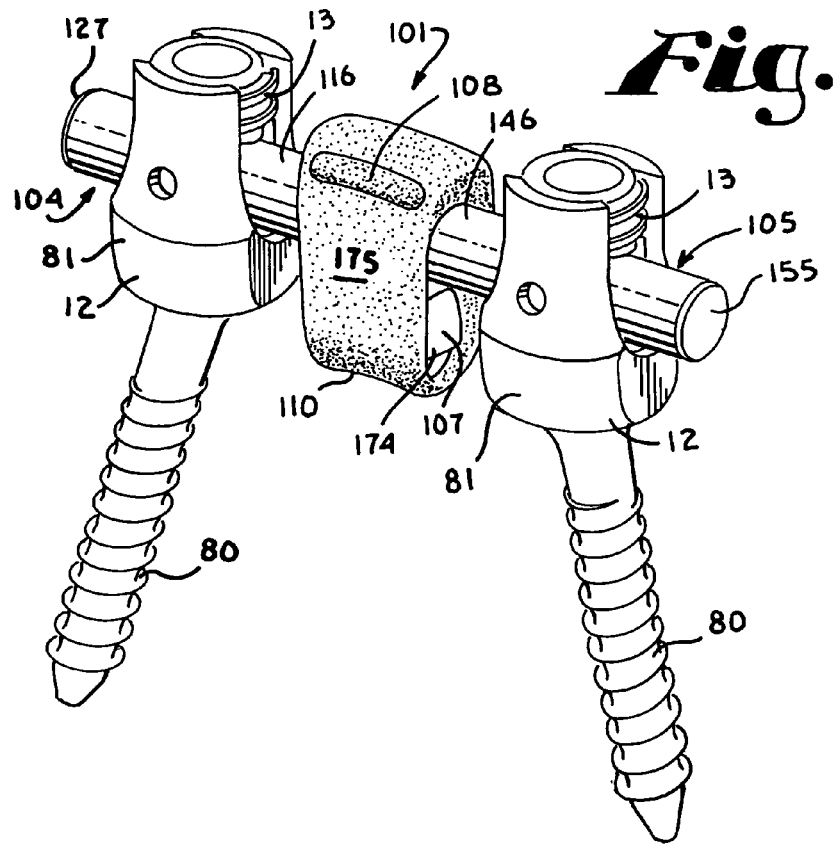
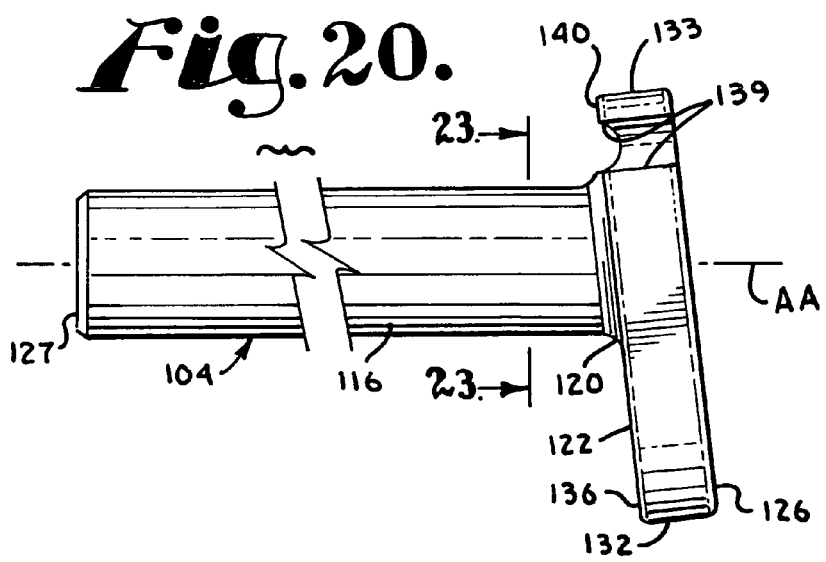

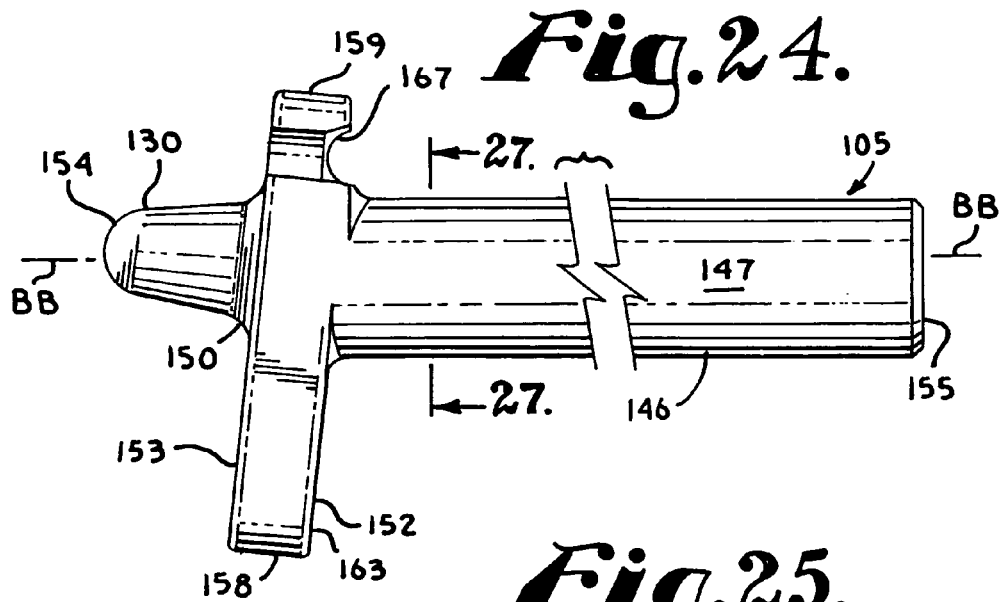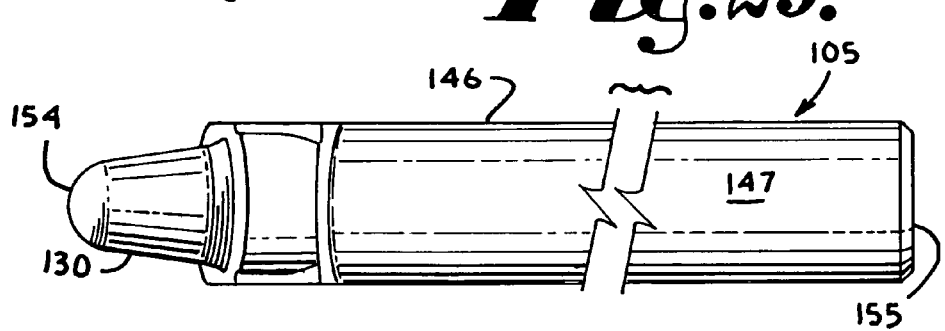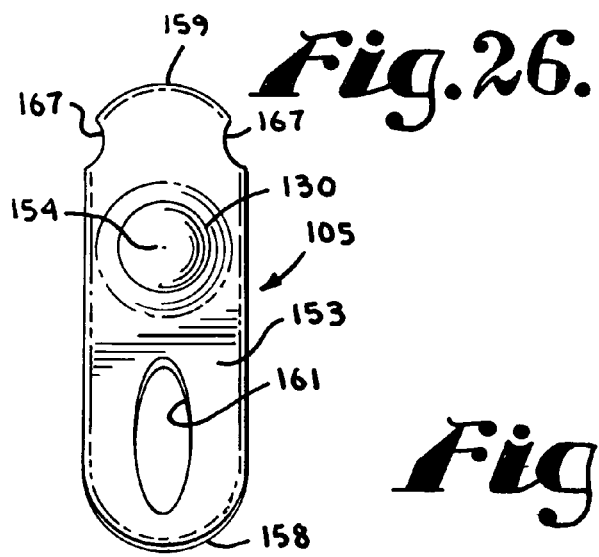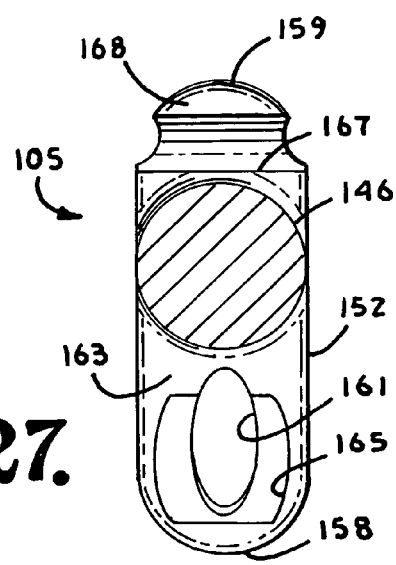

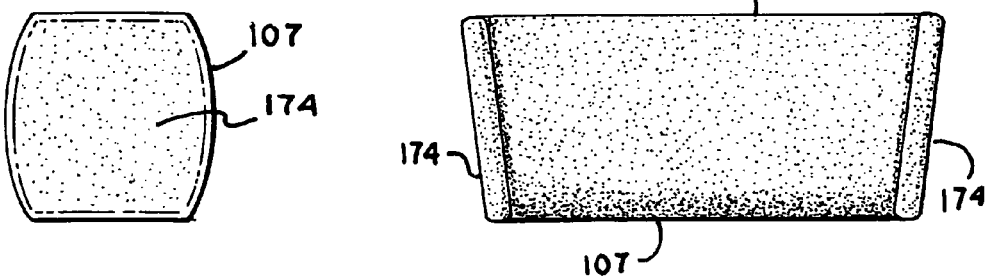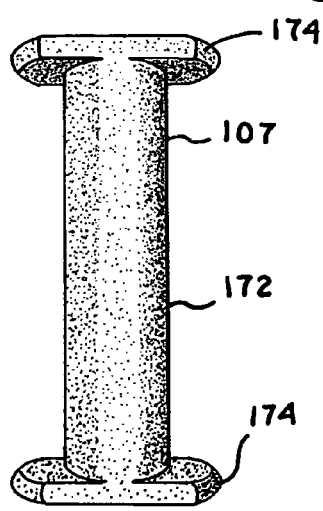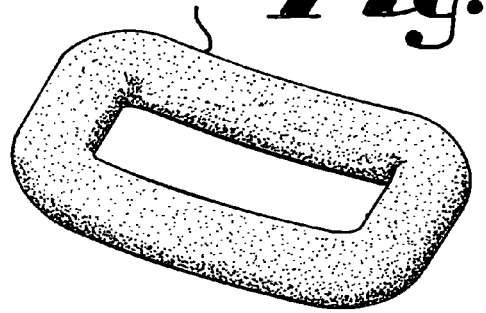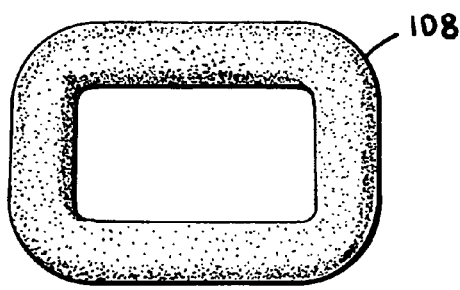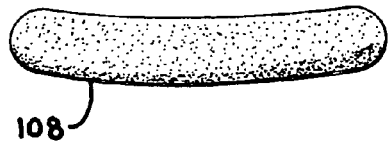

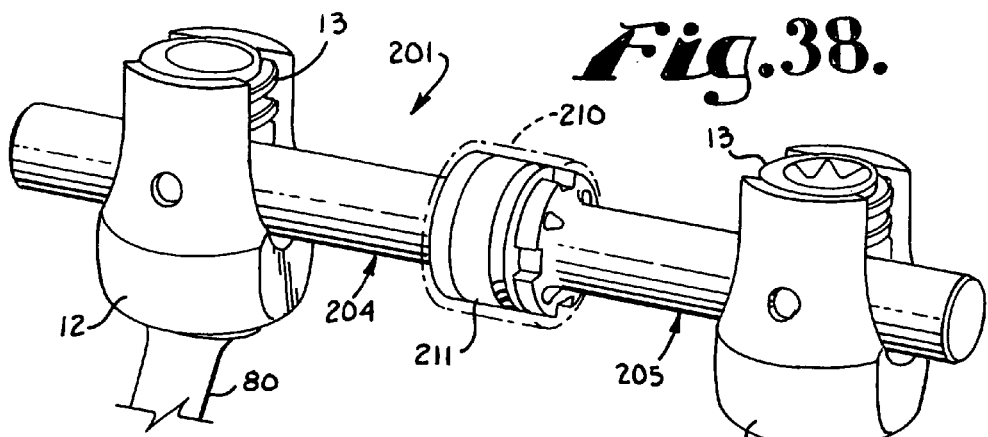
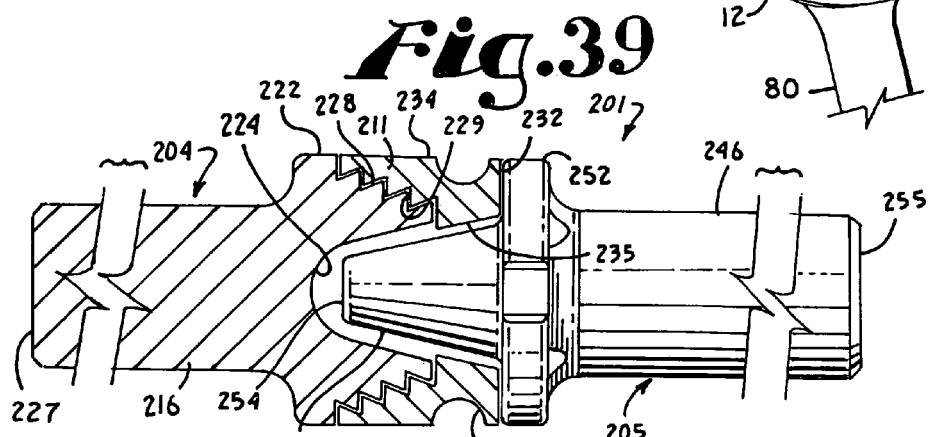
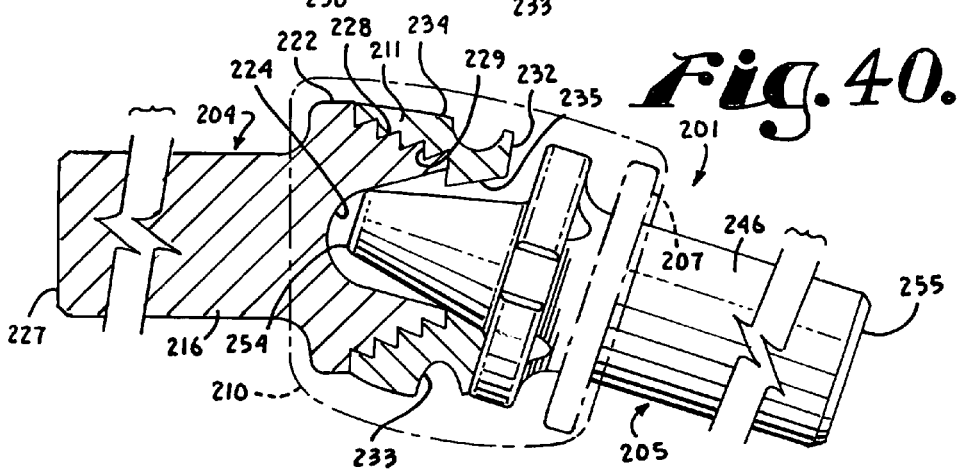

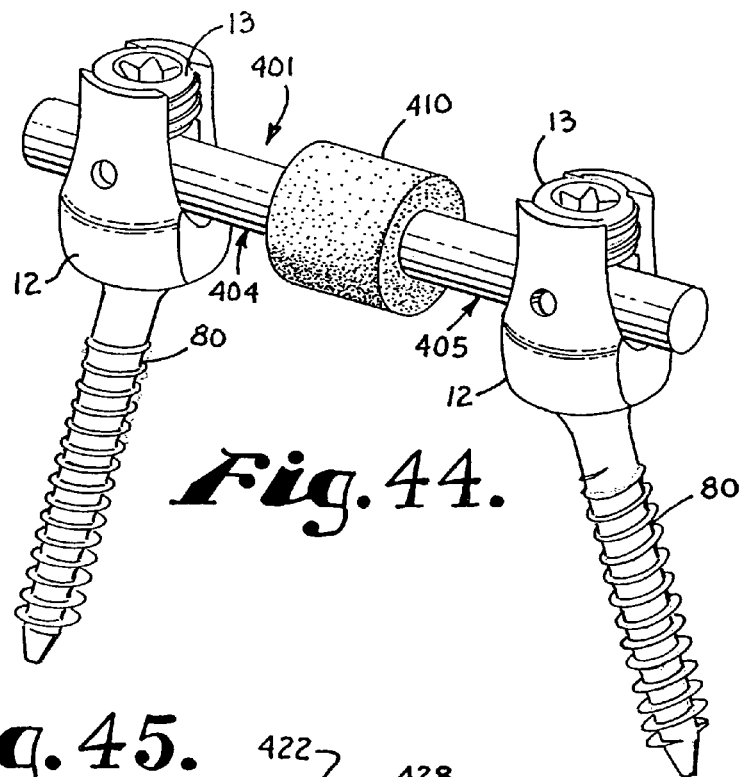
Fig. 44.
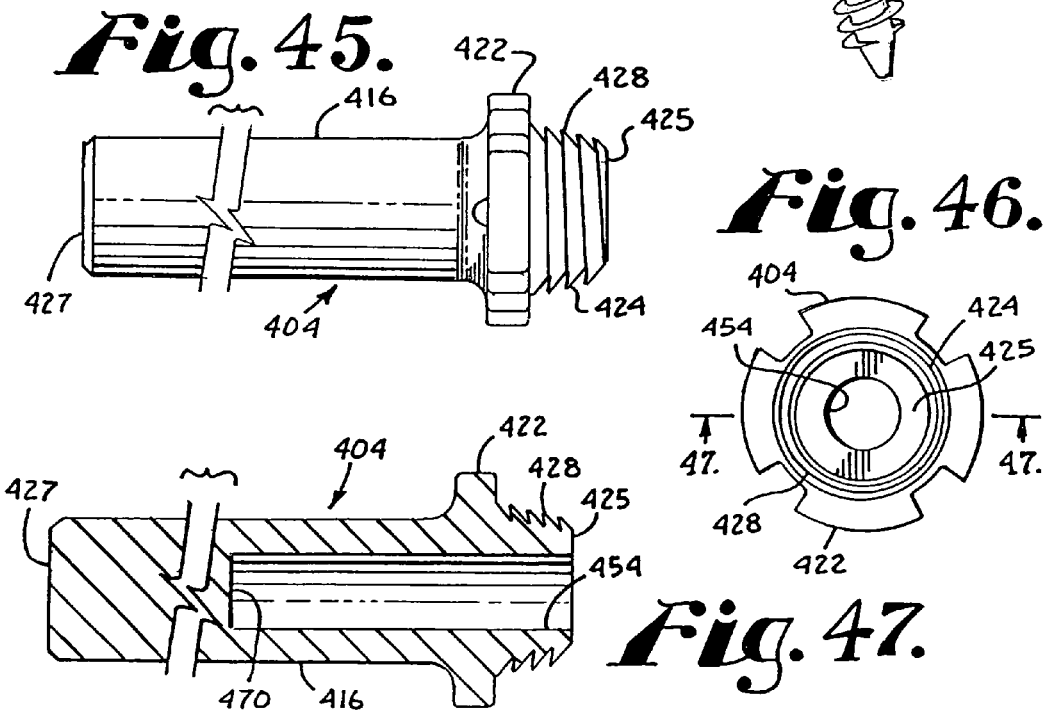
Fig. 45.
Fig. 46.
Fig. 47.

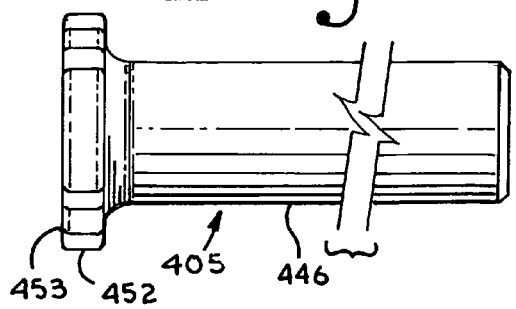
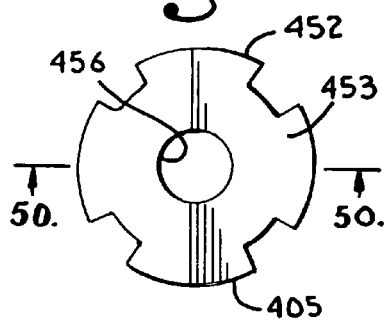
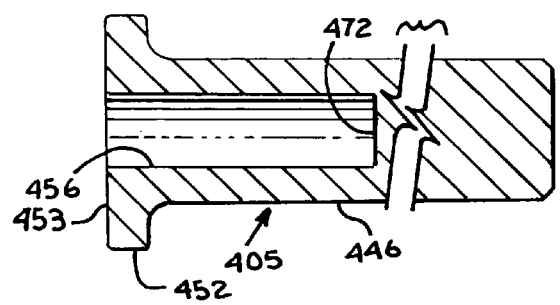
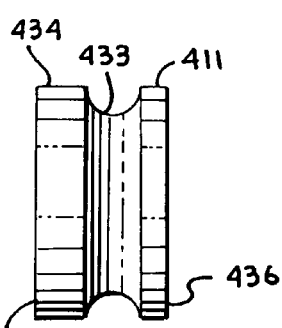
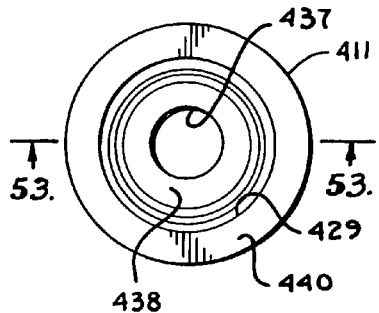
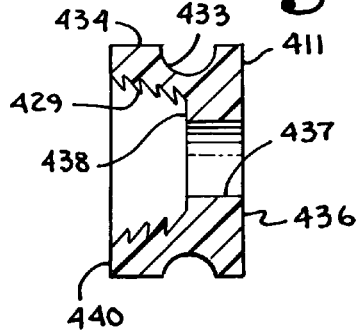

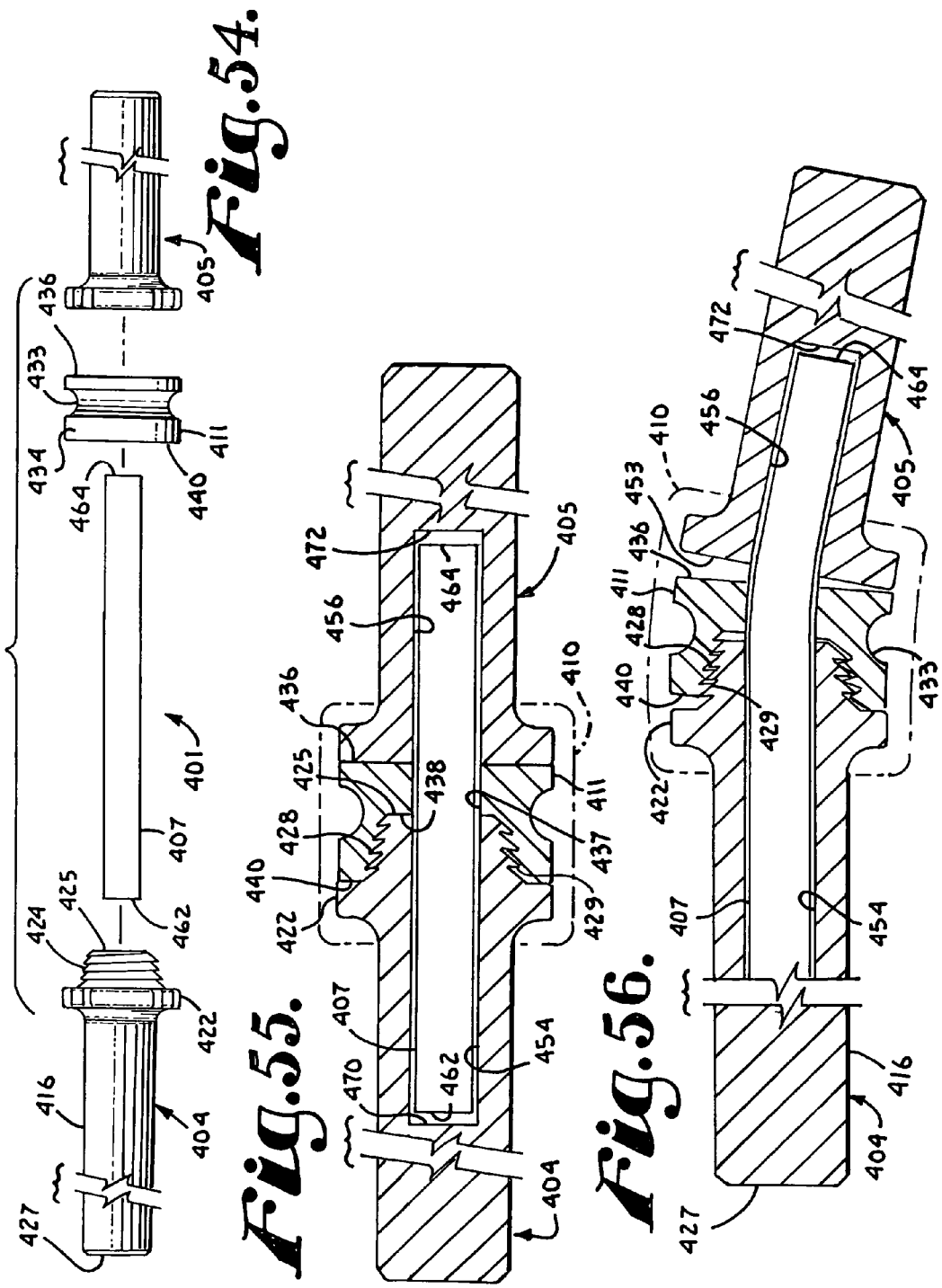

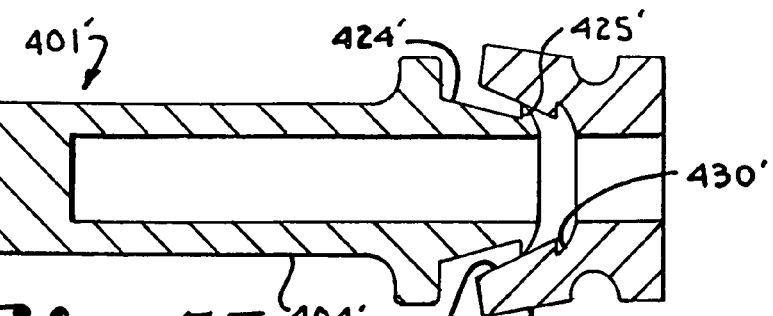
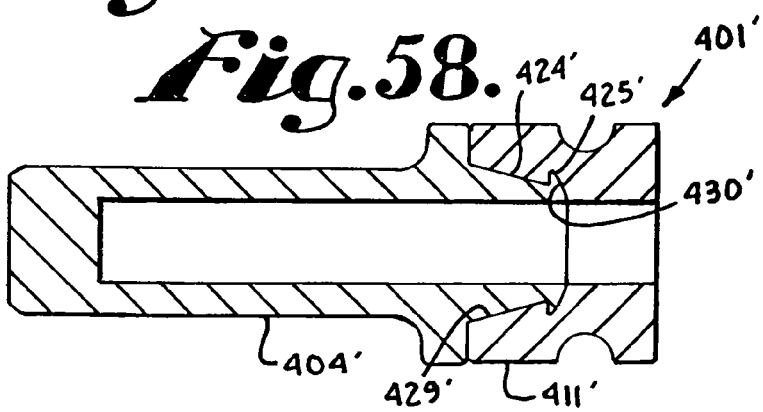
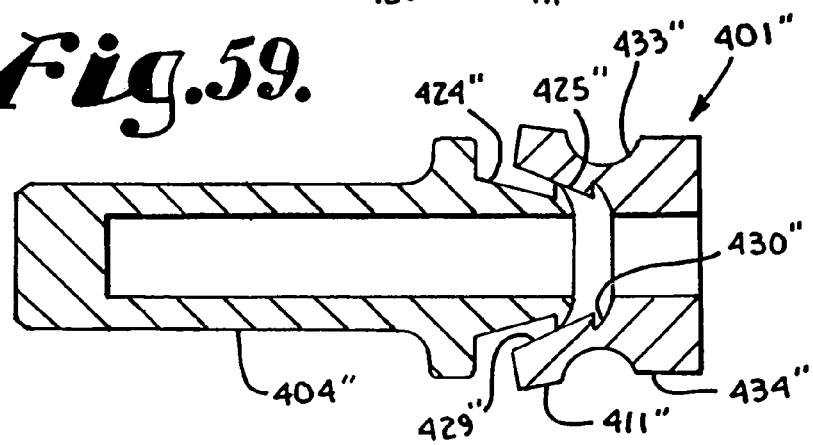
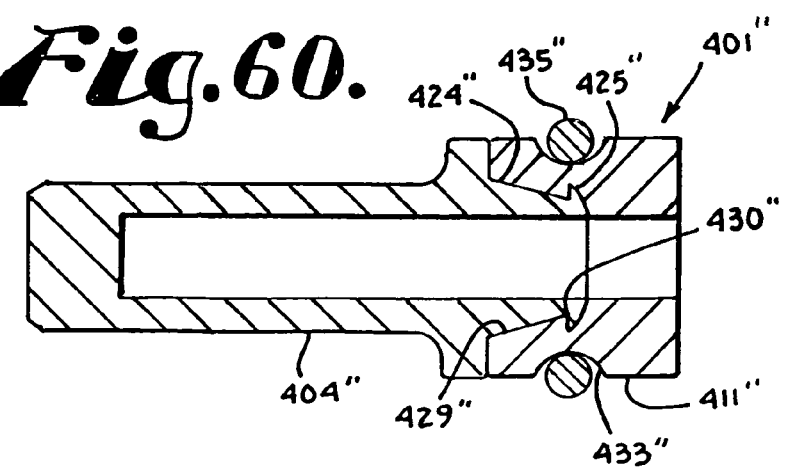

DYNAMIC STABILIZATION ASSEMBLY WITH FRUSTO-CONICAL CONNECTION

CROSS REFERENCE TO RELATED APPLICATIONS

This application claims the benefit of U.S. Provisional Patent Application No. 61/132,911, filed Jun. 24, 2008, which is incorporated by reference herein. This application is also a continuation-in-part of U.S. patent application Ser. No. 12/069,577 filed Feb. 11, 2008 that claims the benefit of U.S. Provisional Patent Application Nos. 60/997,079 filed Oct. 1, 2007 and 60/900,816 filed Feb. 12, 2007, all of which are incorporated by reference herein. This application is also a continuation-in-part of U.S. patent application Ser. No. 12/070,535 filed Feb. 19, 2008 that claims the benefit of U.S. Provisional Patent Application No. 60/902,470 filed Feb. 21, 2007, both of which are incorporated by reference herein. This application is also a continuation-in-part of U.S. patent application Ser. No. 12/287,035 filed Oct. 3, 2008 that claims the benefit of U.S. Provisional Patent Application No. 60/999,965 filed Oct. 23, 2007, both of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the cord or strand in the bone anchors. Although flexible, the cords or strands utilized in such systems typically do not allow for elastic distraction of the system once implanted because the cord or strand must be stretched or pulled to maximum tension in order to provide a stable, supportive system. Such tensioned cord and spacer systems may also cause facet joint compression during spinal movement, especially flexion.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

A longitudinal connecting member assembly according to the invention includes first and second elongate sections, each section attaching to at least one bone anchor. At least one of the sections has a tapered or frusto-conical end portion disposed in spaced relation with the other section. The first and second sections are held in spaced relation by an elastic spacer that substantially surrounds the tapered or frusto-conical portion. According to some embodiments of the invention, the tapered or frusto-conical end portion is in spaced relation with a concave or cup-like portion of the other section, with the elastic spacer filling a void between the tapered or frusto-conical portion and the concave or cup-like portion. In some embodiments of the invention, the elastic spacer is also an over-molded feature that grips both of the first and second sections. Connecting member assemblies of the invention may further include reinforcement structures to improve gripping of the molded spacer onto and/or about the first and second sections. Also, in certain embodiments, when operatively connected to a human spine, the first and second sections include plates that are sized and shaped to extend a greater distance in an anterior direction than in a posterior direction with respect to the spine, moving the axis of rotation of the assembly in an anterior direction during certain spinal movements so that it is closer to the physiologic axis of movement, advantageously off-loading facet joints located adjacent to the spacer. Such off-set or footed plates may further include an anterior tether or keel and a posterior band, the keel and/or band further providing torsion control. In further embodiments of the invention, a floating pin or core extends partially through and between the first and second sections and the elastic spacer or spacers.

OBJECTS AND ADVANTAGES OF THE INVENTION

An object of the invention is to provide dynamic medical implant stabilization assemblies having longitudinal connecting members that include a flexible portion that can resist shear forces and that can allow for controlled bending, torsion, compression and distraction of the assembly. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion integral with the flexible portion. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged perspective view of a dynamic fixation connecting member assembly according to the invention including first and second elongate sections, an over-molded spacer, and first and second reinforcement structures (not shown; covered by the spacer in this view), the assembly shown with a pair of bone screws.

FIG. 2 is an enlarged and partial front elevational view of the first section of the connecting member assembly of FIG. 1.

FIG. 3 is an enlarged side elevational view of the first section of the connecting member assembly of FIG. 1.

FIG. 4 is a cross-sectional view taken along the line 4-4 of FIG. 3.

FIG. 5 is an enlarged and partial front elevational view of the second section of the connecting member assembly of FIG. 1.

FIG. 6 is an enlarged side elevational view of the second section of the connecting member assembly of FIG. 1.

FIG. 7 is a side elevational view of one of the reinforcement structures of the assembly of FIG. 1.

FIG. 8 is a front elevational view of the reinforcement structure of FIG. 7.

FIG. 9 is an enlarged and partial front elevational view of the assembly of FIG. 1 shown prior to addition of the reinforcement structures and the over-molded spacer and shown with portions broken away to show the details of the first and second sections.

FIG. 10 is a reduced partial front elevational view, similar to FIG. 9, showing the first reinforcement structure in position on the first section and the second reinforcement structure prior to being placed in position on the second section, the final position of the second reinforcement structure shown in phantom and prior to the addition of the over-molded spacer.

FIG. 11 is a partial front elevational view, similar to FIG. 10, showing both reinforcement structures in position and the over-molded spacer in phantom.

FIG. 12 is a side elevational view of the assembly of FIGS. 1 and 11.

FIG. 15 is a reduced partial front elevational view of the assembly of FIG. 1 with portions of the first and second sections and the reinforcement structures shown in phantom, the bone screws being in partial front elevation and showing the assembly in a spinal neutral, non-bent operative position.

FIG. 16 is a partial front elevational view, similar to FIG. 15, showing the assembly in an angled or bent orientation as would occur with spinal extension of about fifteen degrees.

FIG. 17 is a partial front elevational view, similar to FIG. 15, showing the assembly in an angled or bent orientation as would occur with spinal flexion of about fifteen degrees.

FIG. 19 is an enlarged perspective view of a second embodiment of a dynamic fixation connecting member assembly according to the invention including a first elongate section with a first off-set plate and a second elongate section with a second off-set plate, an anterior keel, a posterior band and an over-molded spacer, the assembly shown with a pair of bone screws.

FIG. 20 is an enlarged and partial front elevational view of the first section and integral off-set plate of the connecting member assembly of FIG. 19.

FIG. 24 is an enlarged and partial front elevational view of the second section and off-set plate of the connecting member assembly of FIG. 19.

FIG. 25 is an enlarged and partial top plan view of the second section and off-set plate of the connecting member assembly of FIG. 19.

FIG. 26 is an enlarged side elevational view of the second section of the connecting member assembly of FIG. 19.

FIG. 27 is a cross-sectional view taken along the line 27-27 of FIG. 24.

FIG. 28 is an enlarged front elevational view of the anterior keel of the connecting member assembly of FIG. 19.

FIG. 29 is an enlarged side elevational view of the anterior keel of the connecting member assembly of FIG. 19.

FIG. 30 is an enlarged top plan view of the anterior keel of the connecting member assembly of FIG. 19.

FIG. 31 is an enlarged perspective view of the posterior band of the connecting member assembly of FIG. 19.

FIG. 32 is an enlarged top plan view of the posterior band of the connecting member assembly of FIG. 19.

FIG. 33 is an enlarged front elevational view of the posterior band of the connecting member assembly of FIG. 19.

FIG. 38 is an enlarged and partial perspective view of a third embodiment of a dynamic fixation connecting member assembly according to the invention including a first elongate section, a second elongate section, an inner spacer and an over-molded spacer shown in phantom, and also shown with a pair of bone screws.

FIG. 39 is an enlarged and partial front elevational view of the assembly of FIG. 38 shown with portions broken away to show the detail thereof and shown without the over-molded spacer and without bone screws.

FIG. 40 is an enlarged and partial front elevational view of the assembly of FIG. 38 shown with the over-molded spacer in phantom and a reinforcement structure in phantom and illustrating the assembly responding to a combination of flexion and compression loads.

FIG. 44 is an enlarged perspective view of a fifth embodiment of a dynamic fixation connecting member assembly according to the invention including a first elongate section with an outer thread, a second elongate section, an inner spacer (not shown) with an inner thread, an over-molded spacer and an inner floating pin (not shown), and also shown with a pair of bone screws.

FIG. 45 is an enlarged and partial front elevational view of the first section of the connecting member assembly of FIG. 44.

FIG. 46 is an enlarged side elevational view of the first section of the connecting member assembly of FIG. 44.

FIG. 47 is a cross-sectional view taken along the line 47-47 of FIG. 46.

FIG. 48 is an enlarged and partial front elevational view of the second section of the connecting member assembly of FIG. 44.

FIG. 49 is an enlarged side elevational view of the second section of the connecting member assembly of FIG. 44.

FIG. 50 is a cross-sectional view taken along the line 50-50 of FIG. 49.

FIG. 51 is an enlarged front elevational view of the inner spacer of the connecting member assembly of FIG. 44.

FIG. 52 is an enlarged side elevational view of the inner spacer of the connecting member assembly of FIG. 44.

FIG. 53 is a cross-sectional view taken along the line 53-53 of FIG. 52.

FIG. 54 is reduced exploded and partial front elevational view of the assembly of FIG. 44, showing the inner spacer and the inner floating pin but not showing the over-molded spacer or the cooperating bone screws.

FIG. 55 is an enlarged and partial front elevational view of the connecting member assembly of FIGS. 44 and 54 shown in a neutral (non-bent) orientation with portions broken away to show the detail thereof and the over-molded spacer shown in phantom.

FIG. 56 is an enlarged and partial front elevational view of the assembly of FIG. 55 with portions broken away to show the detail thereof and the over-molded spacer in phantom, the assembly shown in an angled or bent orientation as would occur in response to spinal flexion.

FIG. 57 is an enlarged and partial front elevational view of a sixth embodiment of a dynamic fixation connecting member assembly according to the invention with portions broken away to show the detail thereof and being substantially similar to the connecting member assembly shown in FIGS. 44-56 with the exception that the threaded first section and threaded inner spacer are replaced by a capped first section and a snap-on inner spacer, the embodiment being shown in an early stage of assembly and without the floating pin.

FIG. 58 is an enlarged and partial front elevational view of the assembly of FIG. 57 with portions broken away to shown the detail thereof and shown in a subsequent stage of assembly.

FIG. 59 is an enlarged and partial front elevational view of a seventh embodiment of a dynamic fixation connecting member assembly according to the invention with portions broken away to show the detail thereof and being substantially similar to the connecting member assembly shown in FIGS. 44-56 with the exception that the threaded first section and threaded inner spacer are replaced by a capped first section, a snap-on inner spacer and a retainer ring (not shown), the embodiment being shown in an early stage of assembly and without the floating pin.

FIG. 60 is an enlarged and partial front elevational view of the assembly of FIG. 59 with portions broken away to shown the detail thereof and shown in a subsequent stage of assembly and with the retainer ring.

DETAILED DESCRIPTION OF THE INVENTION

Figure 13:
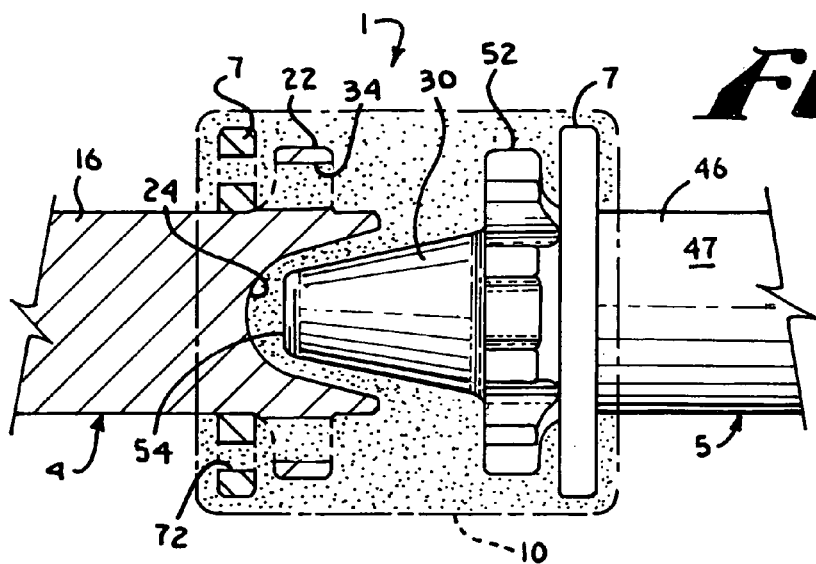
FIG. 13 is an enlarged and partial front elevational view of the assembly of FIG. 1 with portions removed to show the detail thereof and shown in a neutral or non-bent orientation.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-18, the reference numeral 1 generally designates a non-fusion dynamic stabilization longitudinal connecting member assembly according to the present invention. The connecting member assembly 1 includes a first elongate member or segment, generally 4; a second elongate member or segment, generally 5; a pair of optional reinforcement structures 7; and an outer, over-molded elastic spacer 10. The dynamic connecting member assembly 1 cooperates with at least a pair of bone anchors, such as the polyaxial bone screws 12 and cooperating closure structures 13 shown in FIG. 1, the assembly 1 being captured and fixed in place at the segments 4 and 5 by cooperation between the bone screws 12 and the closure structures 13 with the spacer 10 being disposed between the bone screws 12.

The illustrated first and second elongate segments 4 and 5 are each substantially cylindrical and substantially solid, the segment 4 having a central longitudinal axis A and the segment 5 having a central longitudinal axis B. It is foreseen that in some embodiments, the members 4 and 5 may include a small central lumen along an entire length of each section to allow for threading therethrough and subsequent percutaneous implantation of the member 1. As will be described in greater detail below, for molding of the spacer 10 about portions of the segments 4 and 5, the axes A and B are aligned. However, it is foreseen that in other embodiment of the invention, during the molding of the spacer, the axes A and B may be placed at a pre-determined desired angle. It is also noted that rather than being substantially cylindrical, the segments 4 and 5 may each include a variety of cross-sectional shapes (taken perpendicular to the axis A or the axis B), including but not limited to non-circular, such as oval, rectangular, square and other polygonal and curved shapes.

The segments 4 and 5 are preferably made from metal, metal alloys or other suitable materials, including plastic polymers such as polyetheretherketone (PEEK), ultra-high-molecular weight-polyethylene (UHMWP), polyurethanes and composites. The spacer 10 may be made of a variety of materials including natural and synthetic plastics and composites. The illustrated spacer 10 is a molded thermoplastic elastomer, for example, polyurethane or a polyurethane blend; however, any suitable polymer material may be used. The structures 7 may be any of a variety of materials that provide flexible stability and gripping of the elastic surfaces of the spacer 10 about the sections 4 and 5, including, but not limited to metal or metal alloy or polymer mesh, material, weave, strands or solid as shown that may include multiple apertures.

With particular reference to FIGS. 2-4, the first elongate segment 4 includes a substantially solid, smooth and uniform cylinder or rod bone attachment portion 16 having an outer cylindrical surface 17 of circular cross-section, sized and shaped for being received within the polyaxial bone screw 12 as will be described in greater detail below. The illustrated rod portion 16 is sized for receiving one bone screw 12. In other embodiments of the invention, the rod portion 16 may be of a greater length along the axis A to receive two or more bone screws 12. The rod portion 16 may be straight, bent or curved, depending on a desired application. Integral with the rod portion 16 is a connector portion 20 that includes a plate 22 extending radially from the axis A and a concave surface portion 24 formed in an end surface 26 disposed opposite an end surface 27 of the rod portion 16. The illustrated surfaces 26 and 27 are substantially perpendicular to the axis A. The surface 26 runs parallel to and is located near the plate 22. The concave surface portion 24 is substantially symmetrically disposed about the axis A. The illustrated concave surface portion 24 is cup-like in form, sized and shaped to at least partially receive or surround a cone-like or other curved or tapered surface 30 of the elongate member section 5 as will be described in greater detail below. The surfaces 24 and 30 are sized and shaped to be in substantially consistent spaced relation upon molding of the spacer 10 therebetween. Although a cone-in-cup type of relationship is primarily shown in this disclosure, with the "cone" component being frusto-conical, it is noted that other types of cooperating geometry may be used according to the invention. For example, rather than being conical, a polygonal frustum may cooperate with a spaced substantially polygonal or curved recess in an adjacent dynamic section or portion of the assembly. Also, in the illustrated embodiment, the components that make up the elongate section 4: the rod portion 16, the plate 22 and the concave surface 24 are all aligned along the axis A. It is noted however, that in certain embodiments according to the invention, the rod portion 16 may be bent to promote a desired spinal alignment and the plate 22 may be off-set as is illustrated in another illustrated embodiment as described below.

With particular reference to FIG. 3, the illustrated plate 22 includes spaced apertures 34 running parallel to the axis A and spaced therefrom. Furthermore, the plate 22 includes an outer substantially cylindrical surface 36 having notches 38 formed thereon. The illustrated plate 22 includes four spaced circular apertures 34 and four notches 38 spaced between each aperture 34. The plate 22 of the elongate section 4 may include none, one or a plurality of apertures 34 and/or notches 38 to allow for flowing therethrough of the plastic or polymer making up the spacer 10. The spacer 10 thus grips the plate 22 at the surfaces thereof that form the apertures 34 and the notches 38, resulting in an increased polymer gripping surface as compared to a similar plate having fewer or no apertures or notches.

With particular reference to FIGS. 5 and 6, the second elongate segment or member 5 includes a substantially solid, smooth and uniform cylinder or rod bone attachment portion 46 having an outer cylindrical surface 47 of circular cross-section, sized and shaped for being received within the polyaxial bone screw 12 as will be described in greater detail below. The illustrated rod portion 46 is sized for receiving one bone screw 12. In other embodiments of the invention, the rod portion 46 may be of a greater length along the axis B to receive two or more bone screws 12. Integral with the rod portion 46 is a connector portion 50 that includes a plate 52 extending radially from the axis B and the convex frusto-conical surface portion 30 having a curved or flat end portion 54 disposed opposite an end surface 55 of the rod portion 46. The surface portion 30 tapers toward the axis B as it extends away from the plate 52. The illustrated surfaces 54 and 55 are substantially perpendicular to the axis B. The illustrated tapered, substantially frusto-conical surface portion 30 is substantially symmetrically disposed about the axis B. The surface portion 30 is sized and shaped to be received within but not make contact with the cup-like, concave surface portion 24 of the elongate section 4 at any angle of orientation of the elongate section 4 with respect to the elongate section 5. In the illustrated embodiment, the components that make up the elongate section 5: the rod portion 46, the plate 52 and the convex or frusto-conical surface 30 are all aligned along the axis B. It is noted however, that in certain embodiments according to the invention, the rod portion 46 may be bent to promote a desired spinal alignment and the plate 52 may be off-set.

Also with reference to FIGS. 5 and 6, the illustrated plate 52 includes spaced apertures 56 running parallel to the axis B and spaced therefrom. Furthermore, the plate 52 includes an outer substantially cylindrical surface 58 having notches 60 formed thereon. The illustrated plate 52 includes four spaced circular apertures 56 and four notches 60 spaced between each aperture 56. The plate 52 of the elongate section 5 may include none, one or a plurality of apertures 56 and/or notches 60 to allow for flowing therethrough of the plastic or polymer making up the spacer 10. The spacer 10 thus gripping the plate 52 at the surfaces thereof that form the apertures 56 and the notches 60, resulting in an increased polymer gripping surface as compared to a similar plate having fewer or no apertures or notches.

With particular reference to FIGS. 7 and 8, each of the illustrated pair of reinforcement structures or pads 7 includes an outer cylindrical surface 64, and inner cylindrical surface 66, first and second opposed flat annular surfaces 68 and 70 and a plurality of apertures or through bores 72 running through the surfaces 68 and 70. As previously stated, the reinforcement structures 7 are optional and preferably are made from a flexible material having numerous openings, such as a non-metal or metal mesh or weave. The structures 7 may take a variety of forms including but not limited to, woven or meshed materials made from cords, threads, strings, bands, or fibers. The structures 7 may be made from a variety of materials including but not limited to metals, metal alloys (e.g., stainless steel or titanium wires or cables), and polyester fibers. Solid structures with one or more apertures may also be utilized. The inner cylindrical surface 66 is sized and shaped to be received over the rod portions 16 and 46 of the respective elongate members 4 and 5. The outer surface 64 is sized and shaped to correspond approximately in diameter or width to an outer surface 75 of the molded spacer 10 to provide a consistent gripping surface for the polymer, but to be disposed completely within the molded outer surface 75.

The spacer 10 advantageously cooperates with the plates 22 and 52, the concave surface 24 and the convex or cone-like surface 30 to connect the members 4 and 5 and to provide limitation and protection of movement of the assembly 1 between the plates 22 and 52. The over-molded spacer 10 helps keep scar tissue from growing into the structures located between the plates 22 and 52 and also protects patient body tissue from damage that might otherwise occur in that vicinity if over-molding was not present. The spacer 10 is sized and shaped for substantially precise alignment about the connector portions 20 and 50 and between and about the plates 22 and 52. The increased stability and strength of the over-molded assembly 1 advantageously allows for use of a smaller, more compact, reduced volume, lower profile longitudinal connecting member assembly 1 and cooperating bone anchors than, for example, flexible cord and spacer type longitudinal connecting member assemblies or coiled traditional spring-like connecting members.

The illustrated molded spacer 10 is fabricated around and about the portions 20 and 50, the plates 22 and 52 and the reinforcement structures 7 from an initially flowing elastomer, as will be described more fully below, in the presence of the elongate rod portions 16 and 46. The elastomer engages and may adhere to the surfaces 24, 30 and 54, as well as flowing through and setting up within the apertures 34, 56 and 72 and notches 38 and 60. The formed elastomer is substantially cylindrical with an external substantially cylindrical surface 75 that has a slightly larger diameter than diameters of the reinforcement structures 7 and the plates 22 and 52. As illustrated in FIGS. 15-17, the elastic spacer deforms slightly from the substantially cylindrical form shown in FIG. 15 when in a neutral spinal position in response to spinal motion. FIG. 16 illustrates the assembly 1 in response to spinal extension and FIG. 17 illustrates the assembly 1 in response to spinal flexion. In both flexion and extension, the spacer 10 completely surrounds or covers the connector components 20 and 50 as well as the plates 22 and 52 and the reinforcement structures 7. It is foreseen that in some embodiments, the spacer 10 may be molded to be of square, rectangular or other outer cross-sections including curved or polygonal shapes. The spacer 10 may optionally include one or more outer compression grooves. During the molding process, the sections 4 and 5 are held in spaced relation so that spacer material flows about and between the concave surface 24 and the surfaces 30 and 54 so that in any angle of orientation between the sections 4 and 5, the surfaces 30 and/or 54 do not directly abut against the surface 24, but are always cushioned by some spacer material. The material for the spacer 10 may be sized and made from such materials so as to provide for relatively more or less bendability of the section 4 with respect to the section 5, as well as compressibility and stretchability.

Because the illustrated rod portions 16 and 46 are substantially solid and cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screws 12 each include a shank 80 for insertion into a vertebra (not shown), the shank 80 being pivotally attached to an open receiver or head 81. The shank 80 includes a threaded outer surface and may further include a central cannula or through-bore disposed along an axis of rotation of the shank to provide a passage through the shank interior for a length of wire or pin inserted into the vertebra prior to the insertion of the shank 80, the wire or pin providing a guide for insertion of the shank 80 into the vertebra. The receiver 81 has a pair of spaced and generally parallel arms 85 that form an open generally U-shaped channel therebetween that is open at distal ends of the arms 85. The arms 85 each include radially inward or interior surfaces that have a discontinuous guide and advancement structure mateable with cooperating structure on the closure structure 13. The guide and advancement structure may take a variety of forms including a partial helically wound flangeform, a buttress thread, a square thread, a reverse angle thread or other thread like or non-thread like helically wound advancement structure for operably guiding under rotation and advancing the closure structure 13 downward between the receiver arms 85 and having such a nature as to resist splaying of the arms 85 when the closure 13 is advanced into the U-shaped channel. For example, a flange form on the illustrated closure 13 and cooperating structure on the arms 85 is disclosed in Applicant's U.S. Pat. No. 6,726,689, which is incorporated by reference herein.

The shank 80 and the receiver 81 may be attached in a variety of ways. For example, a spline capture connection as described in U.S. Pat. No. 6,716,214, and incorporated by reference herein, is used for the embodiment disclosed herein. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the rod portions 16 and 46 or may include compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. Furthermore, although the closure structure 13 of the present invention is illustrated with the polyaxial bone screw 12 having an open receiver or head 81, it foreseen that a variety of closure structure may be used in conjunction with any type of medical implant having an open or closed head, including monoaxial bone screws, hinged bone screws, hooks and the like used in spinal surgery.

To provide a biologically active interface with the bone, the threaded shank 80 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

In use, at least two bone screws 12 are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula of the bone screw shank 80 and provides a guide for the placement and angle of the shank 80 with respect to the cooperating vertebra. A further tap hole may be made and the shank 80 is then driven into the vertebra by rotation of a driving tool (not shown) that engages a driving feature at or near a top of the shank 80. It is foreseen that the screws 12 and the longitudinal connecting member 1 can be inserted in a percutaneous or minimally invasive surgical manner.

With particular reference to FIGS. 9-11, the longitudinal connecting member assembly 1 is assembled by first placing the sections 4 and 5 in a jig or other holding mechanism such that the jig frictionally engages the rod portions 16 and 46 and holds the concave surface 22 of the section 4 in a position spaced from the convex surfaces 30 and 54 of the section 5 with the surface 22 completely surrounding the surface 54 and partially surrounding the surface 30. Optionally, reinforcement structures 7 are slid onto the rod portions 16 and 46 and placed in spaced relation with respective plates 22 and 52, followed by fabricating the spacer 10 about and between the surfaces 22, 30 and 54, the plates 22 and 52 and the structures 7. In a preferred method of fabrication of the spacer 10, an elastic, polymeric material flows between and about the components of the assembly 1 located between and about the plates 22 and 52 at room temperature, followed by vacuum cure.

With reference to FIGS. 13-18, the assembly 1 is eventually positioned in an open or percutaneous manner in cooperation with the at least two bone screws 12 with the spacer 10 disposed between the two bone screws 12 and the rod portions 16 and 46 each within the U-shaped channels of the two bone screws 12. A closure structure 13 is then inserted into and advanced between the arms 85 of each of the bone screws 12. The closure structure 13 is rotated, using a tool (not shown) engaged with the structure 13 until a selected pressure is reached at which point the rod portion 16 or 46 is urged toward, but not completely seated in the U-shaped channels of the bone screws 12. For example, about 80 to about 120 inch pounds pressure may be required for fixing the bone screw shank 80 with respect to the receiver 81 at a desired angle of articulation.

Figure 14:
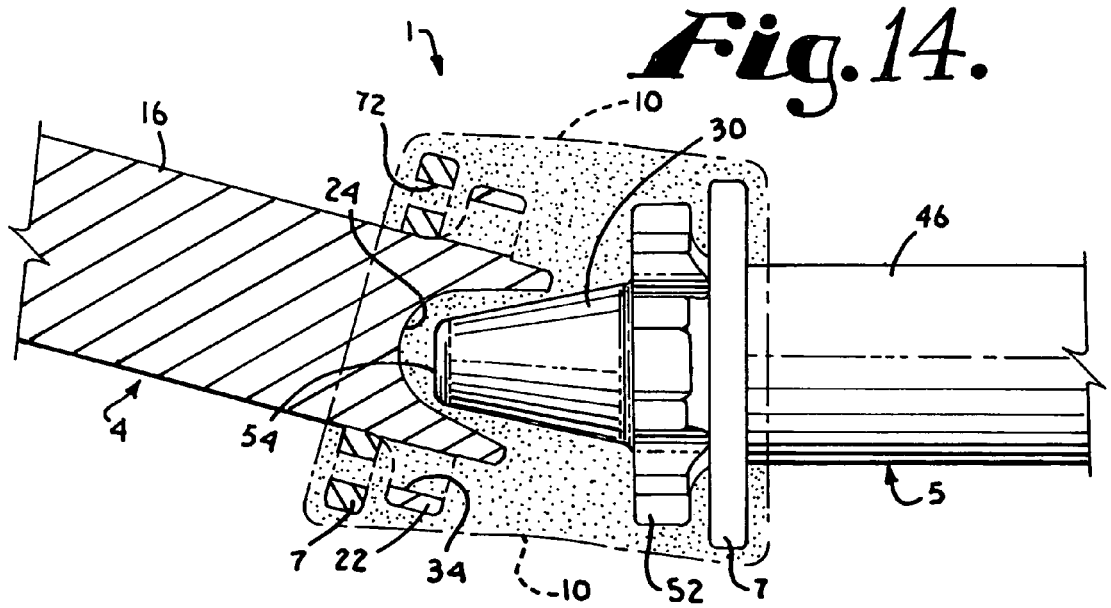
FIG. 14 is an enlarged and partial front elevational view, similar to FIG. 13 showing the first section disposed at an angle with respect to the second section as would occur with spinal extension.
Figure 18:
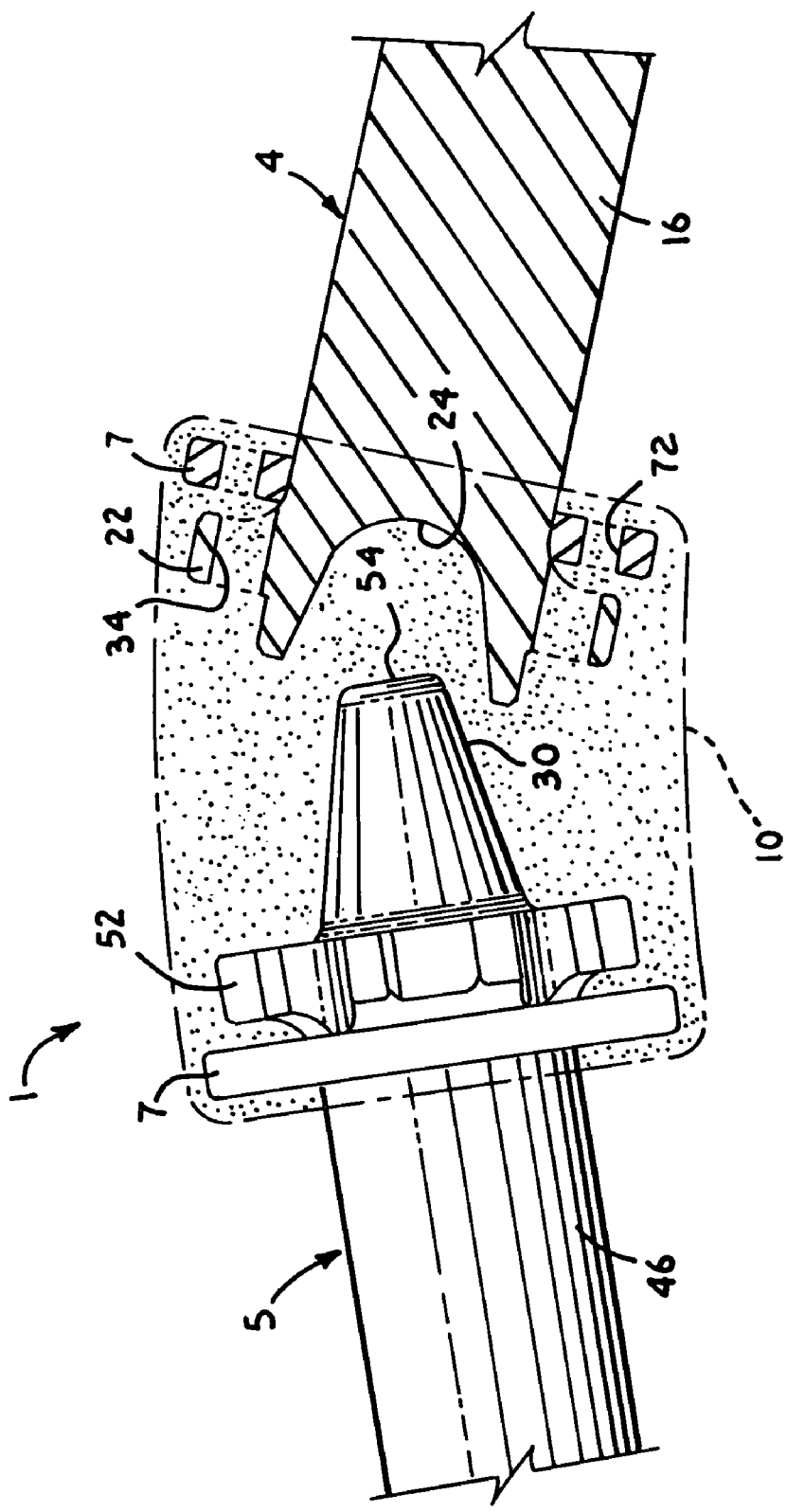
FIG. 18 is an enlarged and partial rear elevational view of the same assembly as FIG. 13, showing the first section disposed at an angle with respect to the second section as would occur with spinal flexion and tension.

As shown in FIGS. 14 and 16, during spinal extension, the assembly 1 is substantially dynamically loaded and oriented relative to the cooperating vertebra, providing relief (e.g., shock absorption) and protected movement with respect to not only extension, but also distractive, compressive, torsional and shear forces placed on the assembly 1 and the two connected bone screws 12. With reference to FIGS. 17 and 18, during spinal flexion, the assembly 1 responds dynamically, also providing relief for distractive, compressive, torsional and shear forces being placed on the assembly 1 during such spinal movement. With particular reference to FIG. 18, the elastic, stretchable and compressible, over-molded spacer 10 is shown stretching as well as bending in response to spinal flexion, advantageously providing a flexion/tension combination that is closer to the physiologic movement of a healthy spine.

If removal of the assembly 1 from any of the bone screw assemblies 12 is necessary, or if it is desired to release the assembly 1 at a particular location, disassembly is accomplished by using the driving tool (not shown) with a driving formation cooperating with the closure structure 13 to rotate and remove the closure structure 13 from the receiver 81. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the rod portions 16 and 46, utilizing the same receivers 81 and the same or similar closure structures 13. Alternatively, if less support is eventually required, a less rigid, more flexible assembly, for example, an assembly 1 made with a more elastic spacer 10, but with end portions having the same diameter as the rod portions 16 and 46, may replace the assembly 1, also utilizing the same bone screws 12.

With reference to FIGS. 19-37, an alternative longitudinal connecting member assembly according to the invention, generally 101 includes a first elongate member or segment, generally 104; a second elongate member or segment, generally 105; an optional anterior keel or tether 107, an optional posterior band 108; and an outer, over-molded elastic spacer 110. The dynamic connecting member assembly 101 cooperates with at least a pair of bone anchors, such as the polyaxial bone screws 12 and cooperating closure structures 13 shown in FIG. 1 and FIG. 19, the assembly 101 being captured and fixed in place at the segments 104 and 105 by cooperation between the bone screws 12 and the closure structures 13 with the spacer 110 being disposed between the bone screws 12.

The illustrated first and second elongate segments 104 and 105 are each substantially cylindrical and substantially solid, the segment 104 having a central longitudinal axis AA and the segment 105 having a central longitudinal axis BB. Similar to the assembly 1, for molding of the spacer 110 about portions of the segments 104 and 105, the axes AA and BB are aligned. However, it is foreseen that in other embodiments of the invention, during the molding of the spacer, the axes AA and BB may be placed at a pre-determined desired angle. It is also noted that rather than being substantially cylindrical, the segments 104 and 105 may each include a variety of cross-sectional shapes (taken perpendicular to the axis AA or the axis BB), including but not limited to non-circular, such as oval, rectangular, square and other polygonal and curved shapes.

Similar to the segments 4 and 5 of the assembly 1, the segments 104 and 105 of the assembly 101 are preferably made from metal, metal alloys or other suitable materials, including plastic polymers such as polyetheretherketone (PEEK), ultra-high-molecular weight-polyethylene (UHMWP), polyurethanes and composites. The elastic spacer 110 and the elastic band 108 may be made of a variety of materials including natural and synthetic plastics and composites. The illustrated spacer 110 is a molded thermoplastic elastomer, for example, polyurethane or a polyurethane blend; however, any suitable polymer material may be used. The keel may be any of a variety of materials that provide a somewhat flexible but tough connection between the segments 104 and 105, such as plastic polymers including, but not limited to PEEK and UHMWP.

With particular reference to FIGS. 20-23, the first elongate segment 104 includes a substantially solid, smooth and uniform cylinder or rod bone attachment portion 116 having an outer cylindrical surface 117 of circular cross-section, sized and shaped for being received within the polyaxial bone screw 12 as will be described in greater detail below. The illustrated rod portion 116 is sized for receiving one bone screw 12. In other embodiments of the invention, the rod portion 116 may be of a greater length along the axis AA to receive two or more bone screws 12. The rod portion 116 may be straight, bent or curved, depending on a desired application. Integral with the rod portion 116 is a connector portion 120 that includes an integral off-set plate 122 and a concave surface portion 124 formed in an end surface 126 disposed opposite an end surface 127 of the rod portion 116.

The illustrated surface 126 is substantially perpendicular to the axis AA. However, the plate 122 and the plate surface 125 are disposed at on obtuse angle with respect to the axis AA. The surface 126 is substantially flat and defines a periphery of the plate 122. The contoured concave or cup-like surface 124 is formed in the surface 126 and is substantially symmetrically disposed about the axis AA. The surface 127 is shaped to at least partially receive or surround a cone-like or other curved, convex surface 130 of the elongate member section 105 as will be described in greater detail below. The surfaces 124 and 130 are sized and shaped to be in spaced relation upon molding of the spacer 110 therebetween.

Figure 22:
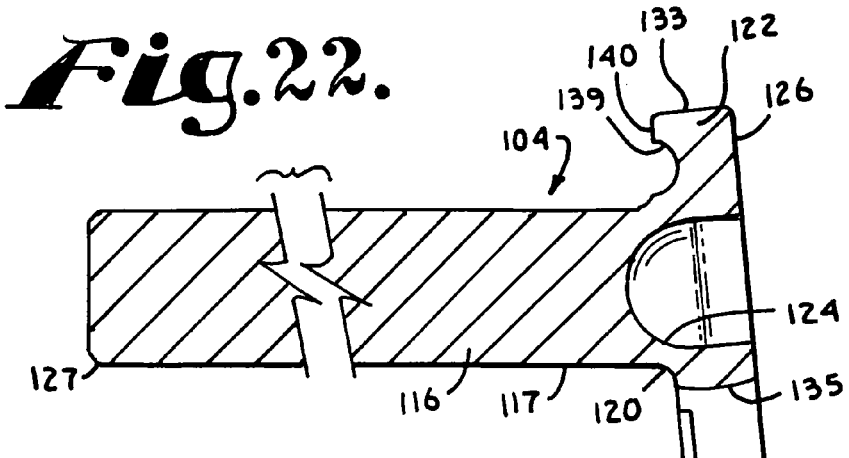
FIG. 22 is a partial cross-sectional view taken along the line 22-22 of FIG. 21.
Figure 21:
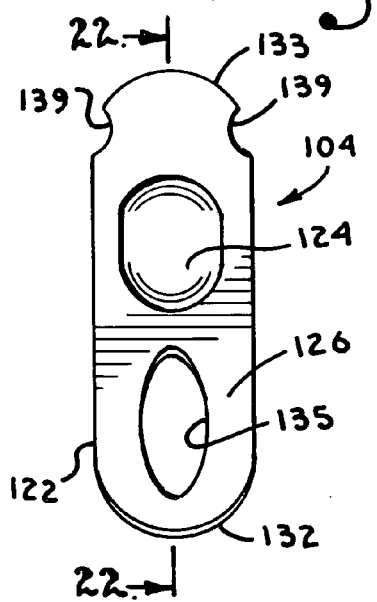
FIG. 21 is an enlarged side elevational view of the first section of the connecting member assembly of FIG. 19.
Figure 23:
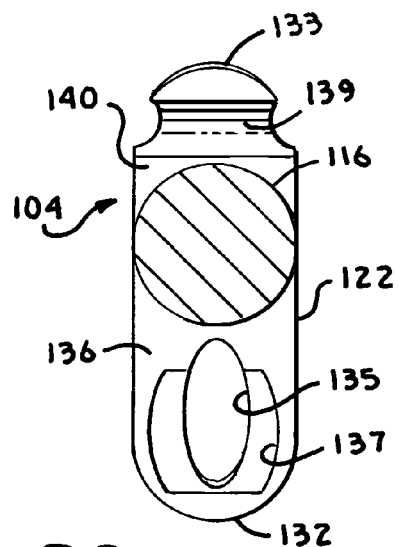
FIG. 23 is a cross-sectional view taken along the line 23-23 of FIG. 20.

The illustrated off-set plate 122 includes an anterior curved surface 132 and an opposed posterior curved surface 133. A distance between the axis AA and the anterior surface 132 is greater than a distance between the posterior surface 133 and the axis AA. In other words, when in an operative position, the plate 122 extends a greater distance in an anterior direction (towards the front of the body), than in a posterior direction. Near the surface 132, a through-bore 135 is formed in the plate 122. The bore 135 is positioned substantially centrally between the surface 132 and the rod portion 116 and extends substantially perpendicular to the surface 126. The surface forming the bore 135 is also curved, having a flared or hour-glass-like shape when viewed in cross-section as illustrated in FIG. 22. The bore 135 is sized and shaped for receiving the keel 107 therethrough as will be described in greater detail below. The illustrated bore 135 has an elliptical or oval shape, but could have a variety of shapes for cooperating with an outer configuration of the keel 107. On a surface 136 disposed opposite the surface 126 and located about a portion of the bore 135, an inset or depression 137 is formed that also cooperates with the keel 107 as will be described in greater detail below.

In the plate 122, near the posterior surface 133 and partially formed in such surface 133 is a groove 139. The groove 139 also is formed into an otherwise flat surface 140 disposed opposite the surface 126 at a posterior portion of the plate 122. The groove 139 is sized and shaped for substantially receiving the elastic posterior band 108 as will be described in greater detail below.

Figure 34:
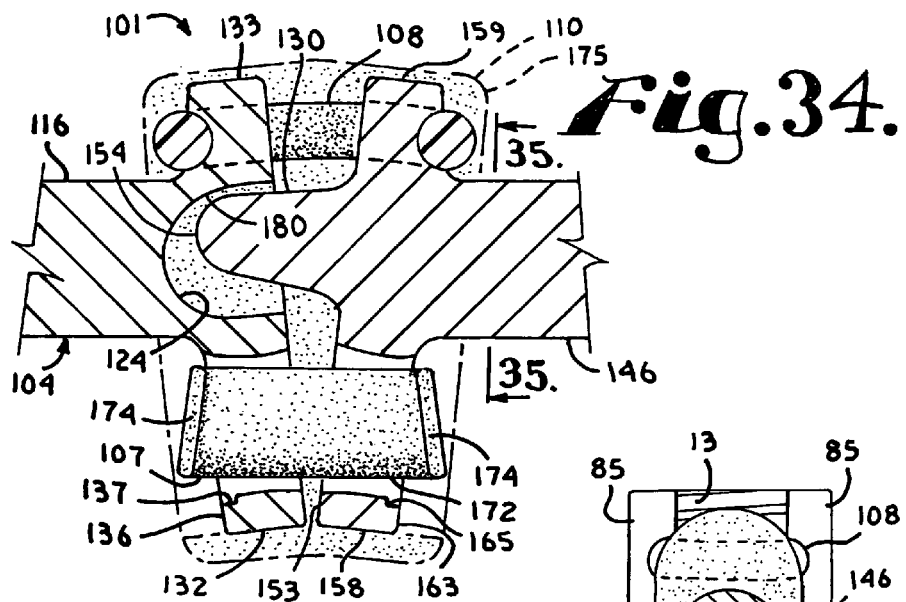
FIG. 34 is an enlarged and partial front elevational view of the connecting member assembly of FIG. 19 shown in a neutral (non-bent) orientation with portions broken away to show the detail thereof.
Figure 35:
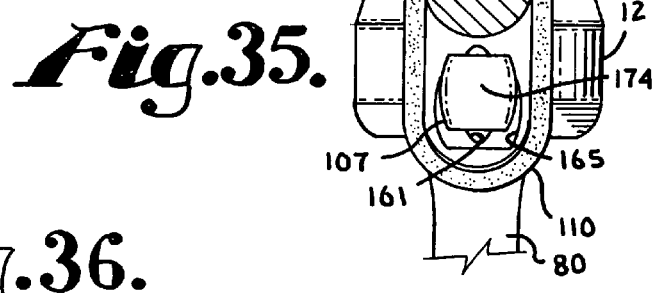
FIG. 35 is a reduced and partial cross-sectional view of the assembly of FIG. 19 taken along the line 35-35 of FIG. 34.
Figure 36:
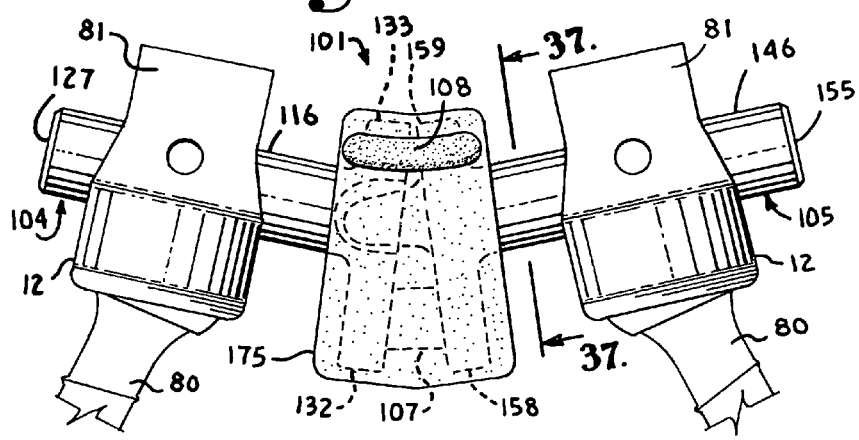
FIG. 36 is an enlarged and partial front elevational view of the assembly of FIG. 19 with portions shown in phantom to show the detail thereof, the assembly shown in an angled or bent orientation as would occur in response to spinal extension.

With particular reference to FIGS. 24-27, the second elongate segment or member 105 includes a substantially solid, smooth and uniform cylinder or rod bone attachment portion 146 having an outer cylindrical surface 147 of circular cross-section, sized and shaped for being received within the polyaxial bone screw 12. The illustrated rod portion 146 is sized for receiving one bone screw 12. In other embodiments of the invention, the rod portion 146 may be of a greater length along the axis BB to receive two or more bone screws 12. Integral with the rod portion 146 is a connector portion 150 that includes an integral off-set plate 152 extending at an obtuse angle from the axis B in both a posterior and an anterior direction, with the plate 152 being longer in the anterior direction, similar to the plate 122. The convex frusto-conical surface portion 130 extends from a substantially planar surface 153 of the plate and is integral with the plate 152, the surface portion 130 having a curved end portion 154 disposed opposite an end surface 155 of the rod portion 146. Unlike the surface portions 30 and 54 of the section 5 of the assembly 1 that are substantially disposed symmetrically about the axis B, the convex surface portions 130 and 154 are not substantially symmetrically disposed about the axis BB. Rather, the portions 130 and 154 extend substantially perpendicular to the plate 152 and thus, when in an operative position, generally extend in a posterior direction, forming a slight angle with respect to the axis BB directed posteriorly. The surface portion 130 is sized and shaped to be received partially within but not make contact with the cup-like, concave surface portion 124 of the elongate section 104 at any angle of orientation of the elongate section 104 with respect to the elongate section 105. However, as best illustrated in FIG. 34 and discussed in greater detail below, the convex end portion 154 of the cone-like portion 130 is molded in place within the spacer 110 material and at least partially surrounded by the concave portion 124 of the section 104 in an off-set or off-center posteriorly directed location within the concave portion 124 in order to enhance stability and flexibility of the spine in extension as shown in FIG. 36 and allow for translation of an axis of rotation of the assembly 101 in an anterior direction in extension and posterior direction in flexion.

The illustrated off-set plate 152 includes an anterior curved surface 158 and an opposed posterior curved surface 159. A distance between the axis BB and the anterior surface 158 is greater than a distance between the posterior surface 159 and the axis BB. In other words, when in an operative position, the plate 152 extends a greater distance in an anterior direction (towards the front of the body), than in a posterior direction. The surfaces 158 and 159 are spaced from one another a same or similar distance as are the surfaces 132 and 133 of the plate 122. Near the surface 158, a through-bore 161 is formed in the plate 152. The substantially oval bore 161 is identical or substantially similar to the bore 135 formed in the plate 122. The bore 161 is positioned substantially centrally between the surface 158 and the rod portion 146 and extends substantially perpendicular to the surface 153. The surface forming the bore 161 is also curved, having a flared or hour-glass-like shape when viewed in cross-section. The bore 161 is sized and shaped for receiving the keel 107 therethrough as will be described in greater detail below. The illustrated bore 161 has an elliptical or oval shape, but could have a variety of shapes for cooperating with an outer configuration of the keel 107. On a surface 163 disposed opposite the surface 153 and located about a portion of the bore 161, an inset or depression 165 is formed that also cooperates with the keel 107 as will be described in greater detail below.

In the plate 152, near the posterior surface 159 and partially formed in the surface 159 is a groove 167. The groove 167 also is formed into an otherwise flat surface 168 disposed opposite the surface 153 at a posterior portion of the plate 152. The groove 167 is sized and shaped for substantially receiving the elastic posterior band 108 as will be described in greater detail below.

With reference to FIGS. 28-30, the illustrated keel or anterior tether 107 includes an elongate body portion 172 and a pair of opposed end portions or stops 174. The end portions 174 are wider than the body portion 172. As best illustrated in FIGS. 34-37, the keel 107 is sized and shaped to extend between the plates 122 and 152, with the end portions or stops 174 disposed at outer surfaces 136 and 163 of the plates 122 and 152, respectively. The illustrated keel body 172 is uniformly sized and shaped to be slidingly received through each of the bores 135 and 161. In particular, when the assembly 1 is in an operative position and flexed during spinal extension, the stops 174 are sized and shaped so as to be disposed within the inset or recessed areas 137 and 165 of the respective plates 122 and 152. It is noted that the keel may be made of a variety of materials, with a tough polymeric material as illustrated in the drawings being only one of the preferred embodiments. In the illustrated embodiment, the keel has enough flexibility that the stops 174 may be manipulated during assembly to be inserted through the through bores 135 and 161. However, in other embodiments of the invention, only one stop or end portion 174 may be utilized and on an opposite end of the keel 107, an aperture or other structure may be placed to allow for the keel to cooperate with a clip or fastener located near the surface 136 or the surface 163 of the plate 122 or the plate 152. Such end that does not have a stop 174 may also be deformed after insertion through the bore 135 or 161. In other embodiments, the keel 107 may be substantially uniform along the length thereof and after extending the keel 107 through the bores 135 and 161, both ends of the keel 107 may be deformed so as to then retain the keel 107 between the plates 122 and 152.

With reference to FIGS. 31-33, the posterior band 108 may be made from a variety of natural and synthetic elastomers. Although the illustrated band 108 is shown having a substantially rectangular shape, the band 108 may otherwise have such flexibility as to not hold a rectangular shape when not inserted about the plates 122 and 152. As shown in FIGS. 19 and 34-37, the band 108 is sized and shaped to snugly fit about the plates 122 and 152 and partially within the grooves 139 and 167, the band 108 being tensioned in a neutral position (see FIG. 34) to an extent that the band 108 remains snugly fitted within the grooves 139 and 167 even during spinal extension as illustrated in FIG. 36. When inserted about the plates 122 and 152 and then partially covered with the elastomer of the spacer 10, the band 108 assists in holding the plates 122 and 152 in spaced relation. During spinal flexion, the band 108 stretches and expands, allowing for protected and controlled spinal movement.

The spacer 110 is substantially similar to the spacer 10 previously described herein with respect to the assembly 1. The spacer 110 advantageously cooperates with the keel 107, the band 108, the plates 122 and 152, the concave surface 124 and the convex or cone-like surface 130 to connect the members 104 and 105 and to provide limitation and protection of movement of the assembly 101 between the plates 122 and 152. The illustrated molded spacer 110 is fabricated around and about the portions 120 and 150, the plates 122 and 152, and portions of the keel 107 and the band 108 from an initially flowing elastomer in the presence of the elongate rod portions 116 and 146. The elastomer engages and may adhere to the surfaces 124, 130 and 154. During molding, the elastomer of the spacer 110 is not allowed to flow through and set up within the through bores 135 and 161 or adhere to the keel 107. The formed elastomer is somewhat trapezoidal in form, having an external surface 175 that is slightly wider and higher than the plates 122 and 152 and extends a length along the assembly 101 between the rod portion 116 and the rod portion 146 such that the plates 122 and 152 are completely surrounded by elastomer. As illustrated, for example, in FIG. 36, the elastic spacer 101 deforms during spinal extension and to a lesser extent during spinal flexion. In both flexion and extension, the spacer 110 completely surrounds or covers the connector components 120 and 150 as well as the plates 122 and 152 and most of the band 108. The spacer 110 may optionally include one or more outer compression grooves. During the molding process, the sections 104 and 105 are held in spaced relation so that spacer material flows about and between the concave surface 124 and the surfaces 130 and 154 so that in any angle of orientation between the sections 104 and 105, the surfaces 130 and/or 154 do not directly abut against the surface 124, but are always cushioned by some spacer material. The material for the spacer 110 may be sized and made from such materials as to provide for relatively more or less bendability of the section 104 with respect to the section 105 and also stretchability and compressibility in response to movement of the sections 104 and 105 toward and away from one another.

With particular reference to FIGS. 19 and 34-37, the longitudinal connecting member assembly 101 is assembled by first placing the sections 104 and 105 in a jig or other holding mechanism such that the jig frictionally engages the rod portions 116 and 146 and holds the concave surface 122 of the section 104 in a position spaced from the convex surfaces 130 and 154 of the section 105 with the surface 122 completely surrounding the surface 154 and partially surrounding the surface 130. As best illustrated in FIG. 34, the rod portions 116 and 146 are aligned, aligning axis AA with axis BB, resulting in the surface portion 154 being directed toward and placed closer to a portion 180 of the surface 124 that is disposed near the plate portion having the groove 139. Optionally, reinforcement structures, such as the structures 7 may also be slid onto the rod portions 116 and 146 as previously described with respect to the rod portions 16 and 46 of the assembly 1. The anterior keel 107 is positioned between the plates 122 and 152 with the end portions or stops 174 being pushed through the through bores 135 and 161 until the stops 174 are disposed outside the surfaces 136 and 163 of the respective plates 122 and 152 and extending beyond the inset portions 137 and 165. Also, prior to molding of the spacer 110, the band 108 is placed about the plates 122 and 152 and into the grooves 139 and 167. Then, the spacer 110 is fabricated about and between the surfaces 122, 130 and 154, the plates 122 and 152 and the band 108. The mold is structured such that resin does not flow into the through bores 135 and 161 and a lumen is created about the keel 107 such that the keel body 172 may freely slide back and forth through both of the bores 135 and 161. In a preferred method of fabrication of the spacer 110, an elastic, polymeric material flows between and about the components of the assembly 101 located between and about the plates 122 and 152 at room temperature, followed by vacuum cure.

With reference to FIGS. 19 and 34-37, the assembly 101 is eventually positioned in an open or percutaneous manner in cooperation with the at least two bone screws 12 with the spacer 110 disposed between the two bone screws 12 and the rod portions 116 and 146 each within the U-shaped channels of the two bone screws 12. A closure structure 13 is then inserted into and advanced between the arms 85 of each of the bone screws 12. The closure structure 13 is rotated, using a tool (not shown) engaged with the structure 13 until a selected pressure is reached at which point the rod portion 116 or 146 is urged toward, but not completely seated in the U-shaped channels of the bone screws 12. For example, about 80 to about 120 inch pounds pressure may be required for fixing the bone screw shank 80 with respect to the receiver 81 at a desired angle of articulation.

Figure 37:
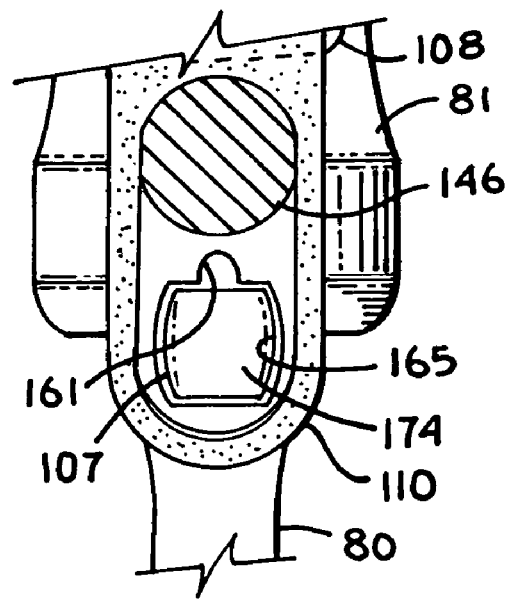
FIG. 37 is a partial cross-sectional view taken along the line 37-37 of FIG. 36.

As shown in FIGS. 36 and 37, during spinal extension, the assembly 101 is substantially dynamically loaded and oriented relative to the cooperating vertebra, providing relief (e.g., shock absorption) and protected movement with respect to not only extension, but also distractive, compressive, torsional and shear forces placed on the assembly 1 and the two connected bone screws 12. The off-set plates 122 and 152 in cooperation with the keel 107 and the spacer 110, allow for anterior translation of the axis of rotation of the assembly 101, advantageously off-loading spinal facet joints during the extension movement. Extension is limited and controlled by the hard stop created by abutment of the keel end portions 174 against the plate inset portions 137 and 165.

As is made apparent by FIG. 34, during spinal flexion, the anteriorly directed plate portions located near the anterior surfaces 132 and 158 and inset portions 137 and 165, push against a small amount or thickness of the spacer 110 located between the plates 122 and 152 at and near such anterior surfaces 132 and 158, such that the plates do not abut. However, translation of the plates 122 and 152 toward one another is quite limited, causing the posterior band 108 to stretch and retract in response to the spinal movement, thus translating the axis of rotation of the assembly 101 in a posterior direction during extension and an anterior direction during flexion. Both the keel 107 and the band 108, as well as the substantially anteriorly placed spacer 110 advantageously provide shear and torsion control during both extension and flexion.

If removal of the assembly 101 from any of the bone screw assemblies 12 is necessary, or if it is desired to release the assembly 101 at a particular location, disassembly is accomplished by using the driving tool (not shown) with a driving formation cooperating with the closure structure 13 to rotate and remove the closure structure 13 from the receiver 81. Disassembly is then accomplished in reverse order to the procedure described previously herein for assembly.

With reference to FIGS. 38-40, another alternative longitudinal connecting member assembly according to the invention, generally 201 includes a first elongate member or segment, generally 204; a second elongate member or segment, generally 205; an optional reinforcement structure 207, an outer, over-molded elastic spacer 210 and in inner spacer 211. The dynamic connecting member assembly 201 cooperates with at least a pair of bone anchors, such as the polyaxial bone screws 12 and cooperating closure structures 13 shown in FIG. 38, the assembly 201 being captured and fixed in place at the segments 204 and 205 by cooperation between the bone screws 12 and the closure structures 13 with the spacers 210 and 211 being disposed between the bone screws 12.

The illustrated first and second elongate segments 204 and 205 are each substantially cylindrical and substantially similar to the respective segments 4 and 5 of the assembly 1 previously described herein, with the exception of a portion of the segment 204. Like the segment 4, the segment 204 includes a rod portion 216, a plate 222 and a concave surface 224 disposed opposite an end 227 of the rod portion 216. Thus the features 216, 222, 224 and 227 are substantially similar to the respective rod portion 16, the plate 22, concave surface 24 and end 27 of the segment 4. Unlike the segment 4, the plate 222 does not include apertures (although it could). Furthermore, extending from the plate 222 and surrounding the concave surface 224 is an outer threaded surface 228. In the illustrated embodiment, the outer surface 228 is frusto-conical in form and includes a single helical thread for threadable mating engagement with an inner threaded surface 229 of the inner spacer 211. The spacer 211 is sized and shaped to substantially bridge between the section 204 and the section 205 when the assembly 201 is in a neutral position as shown in FIG. 39. An end surface 232 of the spacer 211 is disposed near or may abut against the plate 252 of the section 205. The illustrated inner spacer further includes an outer groove 233 extending into and about a substantially cylindrical outer surface 234 of the spacer 211. Extending from the inner threaded surface 229 and toward the plate 252 is an inner partially conical surface 235 sized and shaped to receive a portion of the substantially convex or frusto-conical surface 230 of the section 205.

The elongate segment 205 is identical or substantially similar to the segment 5 of the assembly 1, having a rod portion 246, a plate 252, a convex or frusto-conical surface 230, a flat or convex surface end 254 and an opposite end 255 the same or similar to respective rod portion 46, plate 52, convex surface 30, convex end surface 54 and opposite end 55 of the assembly 1. Identical or similar to the segments 4 and 5 of the assembly 1, the segments 204 and 205 of the assembly 201 are preferably made from metal, metal alloys or other suitable materials, including plastic polymers such as polyetheretherketone (PEEK), ultra-high-molecular weight-polyethylene (UHMWP), polyurethanes and composites. The reinforcement structure 207 is the same or similar in form and function to the structure 7 of the assembly 1.

The elastic outer, over-molded spacer 210 and the elastic inner spacer 211 may be made of a variety of materials including natural and synthetic plastics and composites. The illustrated spacer 210 is a molded thermoplastic elastomer, for example, polyurethane or a polyurethane blend; however, any suitable polymer material may be used. The inner spacer 211 may be any of a variety of materials that are flexible but preferably more tough than the outer spacer 210, such as plastic polymers including, but not limited to PEEK, UHMWP and polycarbonate-urethane (PCU).

The inner spacer 211 is first threadably mated to the section 204, followed, in some embodiments, by insertion of the reinforcement structure 207 on the section 205 and then over-molding of the spacer 210 as previously described with respect to the assembly 1. As illustrated in FIG. 40, during spinal flexion, the elastic outer spacer 210 advantageously bends and compresses in response to the spinal movement. Furthermore, the tougher inner spacer 211 does not compress as easily and readily as the outer spacer 210, providing additional control during flexion, a portion of the surface 232 pressing against the plate 252 and acting as a stop against further flexing movement and protection against over-compression of the spinal facet joints.

Figure 41:
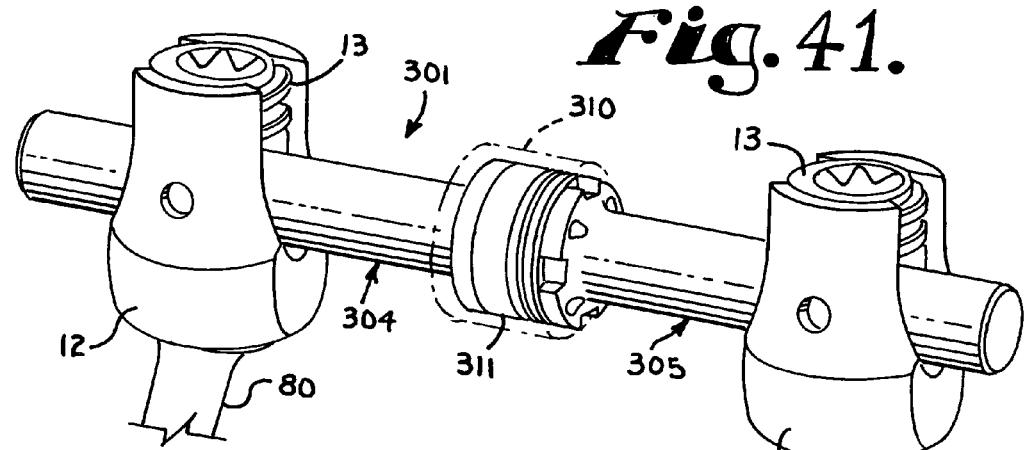
FIG. 41 is an enlarged and partial perspective view of a fourth embodiment of a dynamic fixation connecting member assembly according to the invention including a first elongate section, a second elongate section, an inner spacer and an over-molded spacer shown in phantom, and also shown with a pair of bone screws.
Figure 42:
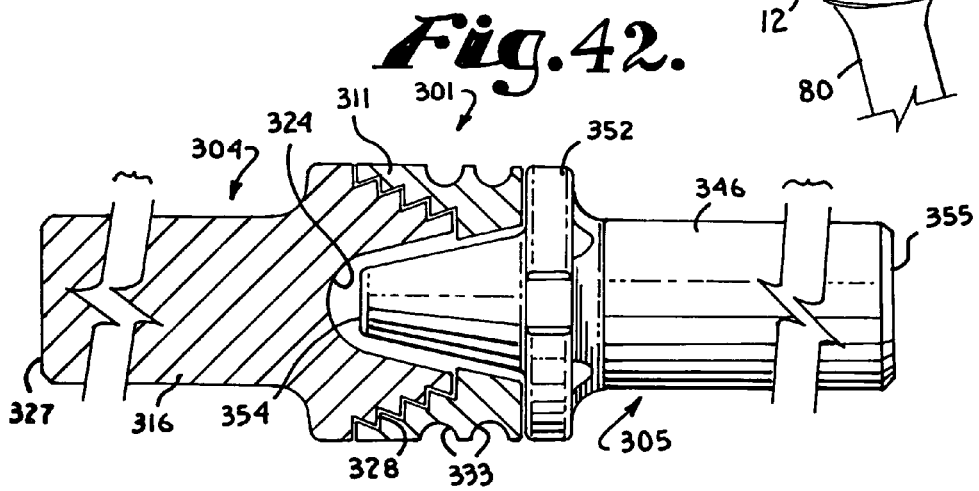
FIG. 42 is an enlarged and partial front elevational view of the fourth embodiment shown in FIG. 41 shown without the over-molded spacer and the bone screws and shown with portions broken away to show the detail thereof.
Figure 43:
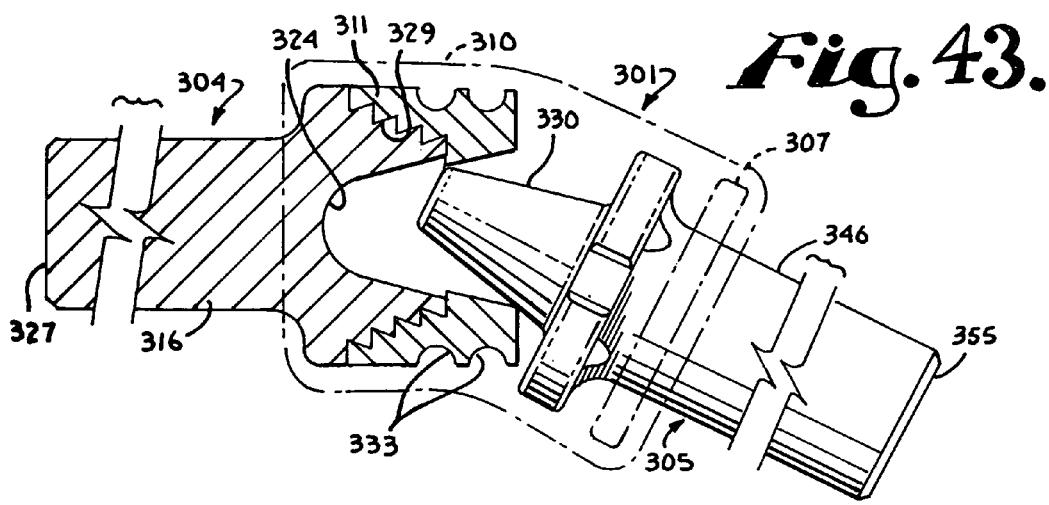
FIG. 43 is an enlarged and partial front elevational view of the assembly of FIGS. 40 and 41 shown with the over-molded spacer in phantom and a reinforcement structure in phantom and illustrating the assembly responding to a combination of flexion and tension loads.

With reference to FIGS. 41-43, another alternative longitudinal connecting member assembly according to the invention, generally 301 includes a first elongate member or segment, generally 304; a second elongate member or segment, generally 305; an optional reinforcement structure 307, an outer, over-molded elastic spacer 310 and in inner spacer 311.

The illustrated assembly 301 is identical to the assembly 201 with the exception that the spacer 311 includes two compression grooves 333 as compared to the single compression groove 233 of the assembly 201. Otherwise the assembly 301 segment 304 includes a rod portion 316 with a concave surface 324, an end surface 327 and an outer threaded surface 328 being the same or similar to the respective rod portion 216, the concave surface 224, the end surface 227 and the threaded surface 228 of the assembly 201. The inner spacer 311 includes an inner threaded surface 329 that is the same of similar to the surface 229 of the spacer 211. The segment 305 includes a convex or frusto-conical surface 330, a rod portion 346, a plate 352 and a convex or flat end 354 and an opposite end 355 the same or similar to the respective convex surface 230, rod portion 246, plate 252, convex surface end 254 and opposite end 255 of the section 205 of the assembly 201. The reinforcement structure 307 is the same or similar to the structure 207 of the assembly 201. The over-molded spacer 310 is the same or similar to the over-molded spacer 210 of the assembly 201 and the spacer 10 of the assembly 1. The spacer 310 completely surrounds portions of the sections 304 and 305, connecting such sections together and completely surrounding the inner spacer 311, the plate 352 and the optional reinforcement structure 307, while also filling in the space between the concave surface 324 and the convex surfaces 330 and 354.

With reference to FIG. 43, the assembly 301 is shown responding to spinal flexion as well as tension, with the outer over-molded spacer 310 both stretching (tensioning) and bending in response to the spinal movement and the inner, tougher spacer 311 functioning as a stop to the bending movement by abutting against opposed surfaces of the frusto-conical portion 330, thus guarding against over compression of the spinal facet joints during flexion/tension of the spine.

With reference to FIGS. 44-56, another alternative longitudinal connecting member assembly according to the invention, generally 401 includes a first elongate member or segment, generally 404; a second elongate member or segment, generally 405; an inner floating pin or core 407, an outer, over-molded elastic spacer 410 and in inner spacer 411. The inner pin 407 is slidingly received in both the segments 404 and 405. The segments 404 and 405 and the pin 407 are preferably made from metal, metal alloys or other suitable materials, including plastic polymers such as polyetheretherketone (PEEK), ultra-high-molecular weight-polyethylene (UHMWP), polyurethanes and composites. Furthermore, in embodiments wherein the segments 404 and 405 are made from a plastic, such as PEEK, the pin 407 may advantageously be made from a material, such as tantalum, to provide an x-ray marker. The pin 407 provides stability to the assembly 401, particularly with respect to torsional and shear stresses placed thereon. The dynamic connecting member assembly 401 cooperates with at least a pair of bone anchors, such as the polyaxial bone screws 12 and cooperating closure structures 13 shown in FIG. 44, the assembly 401 being captured and fixed in place at the segments 404 and 405 by cooperation between the bone screws 12 and the closure structures 13 with the spacers 410 and 411 being disposed between the bone screws 12.

The illustrated first and second elongate segments 404 and 405 are each substantially cylindrical and similar in many respects to the segments 204 and 205 of the assembly 201 previously described herein. With particular reference to FIGS. 45-47, the segment 404 includes a rod portion 416 adjacent to a plate 422, adjacent to a cone-like or frusto-conical portion 424 having a planar end surface 425 disposed opposite an end 427 of the rod portion 416. The cone-like portion 424 includes a helically wound guide and advancement structure, specifically a helically wound reverse buttress thread 428 sized and shaped for mating engagement with an inner helically wound guide and advancement structure or thread 429 of the inner spacer 411. It is noted that a reverse buttress thread was chosen to better resist axial and bending forces that may tend to pull the spacer 411 off of the frusto-conical portion 424. However, other helically wound forms may also be used according to the invention.

As shown in FIGS. 54-56 and with particular reference to FIGS. 51-53, the spacer 411 is substantially cylindrical and tubular in form and is sized and shaped to substantially bridge between the section 404 and the section 405 when the assembly 401 is in a neutral position as shown in FIG. 55. The illustrated inner spacer 411 includes an outer groove 433 extending into and about a substantially cylindrical outer surface 434 of the spacer 411. Extending from the inner threaded surface 429 and towards a planar end surface 436 is a bore 437 sized and shaped to slidingly receive the floating pin 407. A shoulder or shelf 438 is located between the threaded surface 429 and the bore 437, the shoulder 438 being annular and disposed substantially perpendicular to a central axis of the bore 437. Opposite the annular planar surface 436 is an annular planar end surface 440.

With particular reference to FIGS. 48-50, the elongate segment 405 is substantially similar to the segment 205 of the assembly 201, with the exception that it does not include a frusto-conical end portion. The segment 405 includes a rod portion 446 and a plate 452, substantially similar in form and function to the respective rod portion 246 and plate 252 of the segment 205 previously discussed herein with respect to the assembly 201. The plate 452 includes an annular, planar end surface 453.

Formed in the end surface 425 of the segment 404 and also in the end surface 453 of the segment 405 are respective central apertures 454 and 456 that further extend into respective rod portions 416 and 446. The apertures 454 and 456 each extend along a central axis of the assembly 401 and are sized and shaped to slidingly receive the inner core or pin 407 as best shown in FIGS. 55 and 56 and also to provide for an axial length or space greater than a length of the pin 407 so that the pin is free to slide axially with respect to the sections 404 and 405 and the inner spacer 411 after assembly is completed.

The illustrated pin 407 is cylindrical and substantially solid, having a central longitudinal axis that is the same as the central longitudinal axis of the sections 404 and 405. The pin 407 has an end 462 and an opposite end 464. As best shown in FIG. 55, the pin 407 ends 462 and 464 are spaced from respective end surfaces 470 and 472 defining the respective central apertures 454 and 456. It is foreseen that alternatively, an elastomeric cushion may be inserted between the pin end 462 and the surface 470 and the pin end 464 and the surface 472, thus functioning as a further damper to axially directed compressive forces placed on the assembly 401.

The molding process that results in the spacer 410 is typically performed with the assembly 401 being in the aligned, elongate position shown in FIG. 55, so that no polymer attaches to the pin 407 or penetrates into the apertures 454 and 456 or the spacer bore 437, so that the pin 407 remains slidable within the assembly 401 after the over-molding process is complete.

The elastic outer, over-molded spacer 410 and the elastic inner spacer 411 may be made of a variety of materials including natural and synthetic plastics and composites. The illustrated spacer 410 is a molded thermoplastic elastomer, for example, polyurethane or a polyurethane blend; however, any suitable polymer material may be used. The inner spacer 411 may be any of a variety of materials that are flexible but preferably more tough than the outer spacer 410, such as plastic polymers including, but not limited to PEEK, UHMWP and polycarbonate-urethane (PCU).

In use, the inner spacer 411 is mated to the section 404 by mating the helical guide and advancement structures 428 and 429 until the spacer surface 440 abuts against the plate 422. The pin 407 is then inserted into the bore 437 of the inner spacer 411 and the aperture 454 of the section 404. An opposite end of the pin 407 is then inserted into the aperture 456 of the section 405. The section 405 is advanced toward the section 404 until the surface 453 abuts the spacer surface 436, followed by over-molding of the spacer 410 in a manner as previously described with respect to the spacer 10 of the assembly 1. As illustrated in FIG. 56, during spinal flexion and extension, the elastic outer spacer 410 advantageously bends and compresses in response to the spinal movement. Furthermore, the tougher inner spacer 411 does not compress as easily and readily as the outer spacer 410, providing additional control during bending. If bending is accompanied by tension, as shown in FIG. 56, the outer spacer 410 advantageously holds the sections 404 and 405 together, while allowing for movement, with the inner, spacer 411 limiting, but not stopping such movement, the inner spacer 411 at the groove 433 also compressing, if necessary, in response to bending movement.

With reference to FIGS. 57 and 58, a portion of an alternative assembly, generally 401' is shown. The assembly 401' includes a first segment 404' and an inner spacer 411' for use in combination with the second segment 405, floating pin 407 and over-molded spacer 410 previously described herein with respect to the assembly 401. The first segment 404' and the inner spacer 411' are substantially similar in form and function to the respective segment 404 and the inner spacer 411 previously described herein, only differing therefrom with respect to the form and manner of attaching the segment 404' to the spacer 411'. In lieu of the helically-wound or threaded attachment between the segment 404 and the spacer 411, the segment 404' and the spacer 411' have a snap-on connection. As the spacer 411' is typically made from a resilient material, the segment 404' and the spacer 411' are formed such that a portion of the segment 404' engages, is deformed and is then held against or into the spacer 411' after springing back into an original form. Specifically, the segment 404' includes a frusto-conical portion 424' that includes a lipped end surface 425'. The spacer 411' includes an inner frusto-conical surface 429' that further includes a recess 430' for receiving and holding the lipped end surface 425' as best illustrated in FIG. 58.

With reference to FIGS. 59 and 60, a portion of another alternative assembly, generally 401" is shown. The assembly 401" includes a first segment 404" and an inner spacer 411" for use in combination with the second segment 405, floating pin 407 and over-molded spacer 410 previously described herein with respect to the assembly 401. The first segment 404" and the inner spacer 411" are identical or substantially similar to the respective segment 404' and spacer 411' previously discussed herein with respect to the assembly 401'. Thus, the assembly 401" includes a snap-on feature of a frusto-conical portion 424" that includes a lipped end surface 425" and an inner frusto-conical surface 429" that further includes a recess 430" for receiving and holding the lipped end surface 425" as best illustrated in FIG. 60. Furthermore, the spacer 411" includes an outer groove 433" formed in a cylindrical outer surface 434" thereof that receives a retainer ring 435" that aids in holding the spacer 411" against the frusto-conical surface 424" of the section 404". In the illustrated embodiment, the spacer 411" is soft enough for the ring 435" to be slipped over the cylindrical surface 434" until the ring 435" is received in the groove 433". In other embodiments of the invention, the ring 435" may be split or be in the form of an elastic band. Split or open rings may be adhered or spot-welded once located in the groove 433".

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least two bone attachment structures cooperating with a longitudinal connecting member, the improvement wherein the longitudinal connecting member comprises:
    a) a first substantially rigid longitudinal connecting member section having a central axis, the first section having a first bone anchor attachment portion and an end portion tapering towards the central axis;
    b) a second substantially rigid longitudinal connecting member section having a second bone anchor attachment portion, the second section being in spaced relation with the first section;
    c) a molded elastic structure spanning between and attached to both the first and second sections, a molded spacer surrounding the tapered end portion of the first section.

2. The improvement of claim 1 wherein the molded elastic structure is disposed between the first and second sections and holds the first and second sections in spaced relation.

3. The improvement of claim 1 further comprising an elastic spacer fixed to one of the first and second sections, the elastic spacer holding the first and second sections in spaced relation and the molded elastic structure surrounding the elastic spacer.

4. The improvement of claim 3 wherein the elastic spacer is threadably connected to one of the first and second sections.

5. The improvement of claim 3 wherein the elastic spacer is fixed to one of the first and second sections by a snap-on connection.

6. The improvement of claim 1 wherein the second section has an end with a concave surface, the end portion of the first section being in spaced relation with the concave surface.

7. The improvement of claim 6 wherein the molded elastic structure is disposed between the end portion of the first section and the concave surface.

8. The improvement of claim 6 wherein the second section has an outer helical guide and advancement structure and further comprising an elastic spacer having an inner helical guide and advancement structure, the outer guide and advancement structure being mated to the inner guide and advancement structure, fixing the elastic spacer to the second section, the molded elastic structure surrounding the elastic spacer.

9. The improvement of claim 1 wherein the taper of the end portion of the first section has an outer helical guide and advancement structure and further comprising an elastic spacer having an inner helical guide and advancement structure, the outer guide and advancement structure being mated to the inner guide and advancement structure, fixing the elastic spacer to the first section, the molded elastic structure surrounding the elastic spacer.

10. The improvement of claim 1 further comprising an inner floating pin.

11. The improvement of claim 10 wherein the inner floating pin extends into apertures of the first and second connecting member sections.

12. The improvement of claim 1 wherein the first section further comprises a first plate and the second section further comprises a second plate, the first and second plates extending radially from the respective first and second sections, the end portion tapering away from the first plate, the molded elastic structure formed about each of the plates.

13. The improvement of claim 1 further comprising at least one flexible reinforcement structure disposed about at least one of the first and second sections, the molded elastic structure gripping the at least one reinforcement structure.

14. The improvement of claim 1 wherein the first section further comprises a first plate and the second section further comprises a second plate, the first and second plates are each off-set, extending substantially in an operatively anterior direction.

15. The improvement of claim 14 further comprising an elongate anterior keel slidingly cooperating with each of the first and second plates.

16. The improvement of claim 14 further comprising an elastic band surrounding each of the plates, the band located in an operative direction posterior to the first and second sections.

17. In a medical implant assembly having at least two bone attachment structures cooperating with a longitudinal connecting member, the improvement wherein the longitudinal connecting member comprises:
   a) a first longitudinal connecting member section having a first bone anchor attachment portion and a first integral plate with a concave surface formed in an end of the first section located near the plate;
   b) a second longitudinal connecting member section having a second bone anchor attachment portion and a second integral plate with a substantially convex structure extending from the second plate, the convex structure being partially surrounded by the concave surface; and
   c) a molded elastic spacer disposed about the first and second plates and between the concave surface and the convex structure, the spacer gripping both the first and second connecting member sections.

18. The improvement of claim 17 wherein the first and second plates each extend substantially uniformly and radially from the respective first and second sections.

19. The improvement of claim 17 further comprising at least one flexible reinforcement structure disposed about at least one of the first and second sections, the spacer gripping the at least one reinforcement structure.

20. The improvement of claim 17 wherein the first and second plates are each off-set, extending substantially in an operatively anterior direction.

21. The improvement of claim 20 further comprising an elongate anterior keel slidingly cooperating with each of the first and second plates.

22. The improvement of claim 20 further comprising an elastic band surrounding each of the plates, the band located in an operative direction posterior to the first and second sections.

* * * * *